United States Patent [19]

Szajewski et al.

[11] Patent Number: 4,962,018
[45] Date of Patent: Oct. 9, 1990

[54] PHOTOGRAPHIC MATERIALS CONTAINING DIR COMPOUNDS AND PROCESS OF IMAGING

[75] Inventors: Richard P. Szajewski; Jerrold N. Poslusny; Wojciech Slusarek, all of Rochester, N.Y.

[73] Assignee: Eastman Kodak Company, Rochester, N.Y.

[21] Appl. No.: 334,261

[22] Filed: Apr. 6, 1989

Related U.S. Application Data

[63] Continuation-in-part of Ser. No. 209,741, Jun. 21, 1988, abandoned.

[51] Int. Cl.$^5$ .......................... G03C 7/32; G03C 7/26
[52] U.S. Cl. ..................... 430/544; 430/551; 430/553; 430/557; 430/558; 430/957
[58] Field of Search ............... 430/544, 957, 553, 557, 430/558, 551, 505

[56] References Cited

U.S. PATENT DOCUMENTS

| | | | |
|---|---|---|---|
| 3,227,554 | 1/1966 | Barr et al. | 430/505 |
| 4,071,365 | 1/1978 | Usagawa et al. | 430/472 |
| 4,248,962 | 3/1981 | Lau | 430/382 |
| 4,310,621 | 1/1982 | Odenwalder et al. | 430/443 |
| 4,409,323 | 10/1983 | Sato et al. | 430/544 |
| 4,414,308 | 11/1983 | Hamada | 430/505 |
| 4,461,826 | 7/1984 | Yamashita et al. | 430/505 |
| 4,477,563 | 10/1984 | Ichijima et al. | 430/544 |
| 4,524,130 | 6/1985 | Iwasa et al. | 430/505 |
| 4,599,301 | 7/1986 | Ohashi et al. | 430/505 |
| 4,698,297 | 10/1987 | Ichijima et al. | 430/383 |
| 4,812,389 | 3/1989 | Sakanoue et al. | 430/382 |

FOREIGN PATENT DOCUMENTS

| | | |
|---|---|---|
| 789595 | 3/1973 | Belgium . |
| 255085 | 8/1987 | European Pat. Off. . |
| 60-184248 | 11/1985 | Japan . |
| 177548 | 8/1987 | Japan . |
| 2007662 | 4/1978 | United Kingdom . |

OTHER PUBLICATIONS

Research Disclosure, No. 17643, *Research Disclosure*, vol. 176, 1978, Kenneth Mason Publications Ltd., Hampshire, England.

*Primary Examiner*—Paul R. Michl
*Assistant Examiner*—Patrick A. Doody
*Attorney, Agent, or Firm*—Richard E. Knapp

[57] ABSTRACT

A novel photographic development inhibitor releasing coupler (A) comprises a coupler moiety bonded to at least one timing group that enables timing of release of a releasable development inhibitor moiety wherein the releasable development inhibitor moiety contains a —$CH_2$—Q group that is bonded directly to the inhibitor moiety and that is a group enabling, upon exposure and processing of a photographic element containing the coupler, reduced interlayer interimage effect without reduced image acutance. The coupler (A) is useful in a color photographic silver halide element and process.

14 Claims, No Drawings

PHOTOGRAPHIC MATERIALS CONTAINING DIR COMPOUNDS AND PROCESS OF IMAGING

This invention relates to a new photographic coupler that releases a development inhibitor moiety during photographic processing and to photographic materials and processes using such a compound to provide reduced interlayer interimage effect without adversely affecting image acutance.

Various compounds, particularly couplers, are known in the photographic art that are capable of releasing a development inhibitor moiety, such as a mercaptotetrazole moiety. For example, U.S. Pat. No. 4,248,962 describes compounds such as couplers that release a photographically useful group, such as a development inhibitor moiety, by means of an intramolecular nucleophilic displacement reaction in photographic materials. Such compounds provide advantageous image properties. An example of such a compound is:

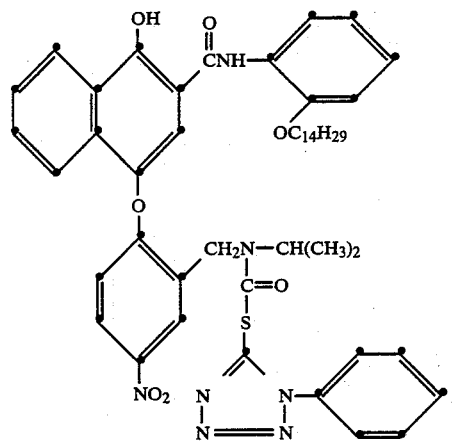

Other couplers that are capable of releasing a development inhibitor moiety (DIR couplers) are also known, such as described in Belgian, Pat. No. 789,595 and U.S. Pat. No. 4,409,323.

A need has existed in color photographic silver halide materials to provide (a) lower interlayer interimage effects demonstrated by reduced development inhibition in adjacent photographic layers without (b) reduced image acutance. This combination of characteristics has not been provided by DIR couplers in the past as illustrated in the following comparative examples.

The present invention solves these problems by providing a photographic element comprising a support bearing at least one photographic silver halide emulsion layer and a development inhibitor releasing coupler (A) comprising a coupler moiety (COUP) bonded to at least one timing group ($T_1$) that enables timing of release of a releasable development inhibitor moiety (INH) wherein the releasable development inhibitor moiety contains a —CH$_2$—Q group that is bonded directly to the inhibitor moiety and that is a group enabling, upon exposure and processing of the element, reduced interlayer interimage effect without reduced image acutance in the emulsion layer. The reduced interlayer interimage effect (IIE) is evidenced typically by a reduced image gamma in the emulsion primarily influenced by the DIR compound relative to the image gamma in another emulsion of the film.

The described coupler (A) enables such advantageous effects preferably in a photographic element comprising at least two photographic silver halide emulsion layers, such as a color photographic silver halide element comprising at least two dye-forming photographic silver halide emulsion layers, or a patterned arrangement of independent elements in one layer such as described in U.S. Pat. No. 3,227,554. The layer arrangement of the photographic element is such that coupler (A) and the development inhibitor moiety (INH) can provide the described advantageous effects. A typical layer arrangement of a photographic element as described comprises on a support at least one red-sensitive silver halide emulsion layer at least one green-sensitive silver halide emulsion layer and at least one blue-sensitive emulsion layer.

The described photographic element preferably comprises at least one dye-forming coupler. A process of developing an image in an exposed photographic element comprising a support bearing a photographic silver halide emulsion comprises the step of developing the element with a silver halide color developing agent in the presence of at least one photographic coupler and at least one coupler (A) as described.

A typical development inhibitor releasing couple (A) as described is represented by the formula:

wherein
COUP is a coupler moiety;
T is a timing group bonded to the coupler moiety at a coupling position and enabling timed release of —INH—CH$_2$—Q from the coupler moiety upon exposure and processing of the element;
INH—CH$_2$—Q is a development inhibitor moiety wherein
Q is a ballasting group enabling the described advantages.
Q is a group (i) having a molecular weight greater than 70 mass units, (ii) containing no ionized groups during processing, (iii) does not substantially decompose during processing, and (iv) contains at least one —C=C— or —C=N— double bond.

An illustrative coupler (A) as described is represented by the formula:

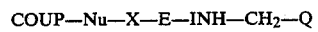

wherein
COUP is a coupler moiety
INH is a development inhibitor moiety containing at least one hetero atom;
Nu is a nucleophilic group attached to COUP at a position from which it is capable of being displaced as a result of reaction of COUP with oxidized color developing agent; p0 X is a linking group spatially relating Nu and E, upon displacement of Nu from COUP, to undergo an intramolecular nucleophilic displacement reaction that cleaves the bond between INH and E;
E is an electrophilic group attached to a hetero atom in INH; and
CH$_2$—Q is a group that enables reduced interlayer interimage effect, evidenced by reduced image gamma as previously described, without reduced image acutance in a color photographic silver halide element.

The described coupler (A) has a key feature that enables reduced interlayer interimage effect evidenced by reduced image gamma as previously described without reduced acutance to be observed in a photographic silver halide element containing such a compound upon exposure and processing. This feature is that the inhibitor moiety with —$CH_2$—Q has reduced transportability in the structure of the photographic element compared to prior art inhibitor moieties containing a simple phenyl group in place of the described —$CH_2$—Q group. The enabling features, among others, of the inhibitor moiety of the invention include: (a) the Q moiety preferably has a molecular weight of greater than 70 mass units, (b) has at least one —C=C— or —C=N— double bond and (c) preferably is not an inhibitor that is decomposed or otherwise destroyed by or in a typical processing solution during photographic processing. The Q group of the inhibitor moiety also preferably contains no ionized groups during photographic processing. A highly preferred INH—$CH_2$—Q moiety that has the described characteristics is a 1-p-methoxybenzyl-5-mercaptotetrazole moiety. This moiety has highly preferred transportability characteristics and is preferred in combination with a timing group (T) that also enables preferred transportability. Such a preferred moiety enables a lower degree of interimage effect and accordingly a lower degree of color correction. But also, this moiety enables an image that has a degree of acutance that is surprisingly high. As a result the coupler (A) enables acutance enhancement as effective as prior DIR couplers, for example those DIR couplers containing phenylmercaptotetrazole as an inhibitor moiety, but without the high interimage effects observed with prior DIR couplers.

The most effective image is observed when the coupler moiety and the inhibitor moiety are separated by a group that enables preferred timing of release of the inhibitor moiety from the carrier moiety during photographic processing. The reaction of coupler (A) with an oxidized color developing agent cleaves the bond between the carrier moiety and the timing group. Then the bond between the timing group and the inhibitor moiety is cleaved by means of an intramolecular nucleophilic displacement reaction enabling the development inhibitor moiety to perform its intended function. Bond cleavage between the timing group and the inhibitor moiety does not involve the action of oxidized color developing agent.

Preferred coupler (A) is represented by the formula as described wherein COUP is a coupler moiety. As used herein the terms "coupler" and "coupler compound" refer to the entire compound, including the coupler moiety, the timing group, and the inhibitor moiety, while the term "coupler moiety" refers to the portion of the compound other than the timing group and the inhibitor moiety.

The coupler moiety can be any moiety that will react with oxidized color developing agent to cleave the bond between the timing group and the coupler moiety. It includes coupler moieties employed in conventional color Forming couplers that yield colorless products as well as coupler moieties that yield colored products on reaction with oxidized color developing agents. Both types of coupler moieties are know to those skilled in the photographic art.

The coupler moiety can be unballasted or ballasted with an oil soluble or fat tail group. It can be monomeric, or it can form part of a dimeric, oligomeric or polymeric coupler, in which case more than one INH group can be contained in the coupler, or it can form part of a bis compound in which the timing and inhibitor groups form part of the link between two coupler moieties.

It will be appreciated that, depending upon the particular coupler moiety, the particular color developing agent and the type of processing, the reaction product of the coupler moiety and oxidized color developing agent can be: (1) colored and nondiffusible, in which case it will remain in the location where it is formed; (2) colored and diffusible, in which case it may be removed during processing from the location where it is formed or allowed to migrate to a different location; or (3) colorless and diffusible or nondiffusible, in which case it will not contribute to image density. In cases (2) and (3) the reaction product may be initially colored and/or nondiffusible but converted to colorless and/or diffusible products during the course of processing.

The timing group is joined to the coupler moiety at any of the positions from which groups released from couplers by reaction with oxidized color developing agent can be attached. Preferably, the timing group is attached at the coupling position of the coupler moiety so that upon reaction of the coupler with oxidized color developing agent the timing group will be displaced. However, the timing group can be in a non coupling position of the coupler moiety from which position it will be displaced as a result of reaction of the coupler with oxidized color developing agent. In the case where the timing group is in a non coupling position of the coupler moiety, other groups can be in the coupling position, including conventional coupling-off groups or the same or different inhibitor moieties from that contained in the described inhibitor moiety of the invention. Alternatively, the coupler moiety can have a timing and inhibitor group in each of the coupling position and a non coupling position. Accordingly, couplers of this invention can release more than one mole of inhibitor per mole of coupler. The inhibitor can be the same or different and can be released at the same or different times and rates.

The timing group can be any organic group which will serve to connect COUP to the inhibitor moiety and which, after cleavage from COUP, will cleave from the inhibitor moiety preferably by an intramolecular nucleophilic displacement reaction of the type described in, for example, U.S. Pat. No. 4,248,962 or by electron transfer down a conjugated chain as described in, for example, U.S. Pat. No. 4,409,323.

As used herein, the term "intramolecular nucleophilic displacement reaction" refers to a reaction in which a nucleophilic center of a compound reacts directly, or indirectly through an intervening molecule, at another site on the compound, which is an electrophilic center, to effect displacement of a group or atom attached to the electrophilic center. Such compounds have a nucleophilic group and electrophilic group spatially related by the configuration the molecule to promote reactive proximity. Preferably the nucleophilic group and the electrophilic group are located in the compound so that a cyclic organic ring, or a transient cyclic organic ring, can be easily formed by an intramolecular reaction involving the nucleophilic center and the electrophilic center.

A useful illustrative class of timing group (T) is represented by the structure:

$-\!(\!-\mathrm{Nu}\!-\!\mathrm{X}\!-\!\mathrm{E}\!-\!)\!-$ wherein:

Nu is a nucleophilic group attached to a position on COUP from which it will be displaced upon reaction of COUP with oxidized color developing agent;

E is an electrophilic group attached to an inhibitor moiety as described and is displaceable therefrom by Nu after Nu is displaced from COUP; and X is a linking group for spatially relating Nu and E, upon displacement of Nu from COUP, to undergo an intramolecular nucleophilic displacement reaction with the formation of a 3 to 7 membered ring and thereby release the inhibitor moiety.

A nucleophilic group (Nu) is understood to be a grouping of atoms one of which is electron rich. This atom is referred to as the nucleophilic center. An electrophilic group (E) is understood to be a grouping of atoms one of which is electron deficient. This atom is referred to as the electrophilic center.

Thus, in photographic couplers as described, the timing group can contain a nucleophilic group and an electrophilic group which are spatially related with respect to one another by a linking group (X) so that upon release from the coupler moiety the nucleophilic center and the electrophilic center will react to effect displacement of the inhibitor moiety rom the timing group. The nucleophilic center should be prevented from reacting with the electrophilic center until release from the coupler moiety and the electrophilic center should be resistant to external attack such as hydrolysis. Premature reaction can be prevented by attaching the coupler moiety to the timing group at the nucleophilic center or an atom in conjunction with a nucleophilic center, so that cleavage of the timing group and the inhibitor moiety from the coupler moiety unblocks the nucleophilic center and permits it to react with the electrophilic center, or by positioning the nucleophilic group and the electrophilic group so that they are prevented from coming into reactive proximity until release. The timing group can contain additional substituents, such as additional photographically useful groups (PUG), or precursors thereof, which may remain attached to the timing group or be released.

It will be appreciated that in the timing group, for an intramolecular reaction to occur between the nucleophilic group and the electrophilic group, the groups should be spatially related after cleavage from the coupler, so that they can react with one another. Preferably, the nucleophilic group and the electrophilic group are spatially related within the timing group so that the intramolecular nucleophilic displacement reaction involves the formation of a 3 to 7 membered ring, most preferably a 5 or 6 membered ring.

It will be further appreciated that for an intramolecular reaction to occur in the aqueous alkaline environment encountered during photographic processing, the thermodynamics should be such and the groups be so selected that the Free energy of ring closure plus the bond energy of the bond formed between the nucleophilic group and the electrophilic group is greater than the bond energy between the electrophilic group and other groups. Not all possible combinations of nucleophilic group, linking group, and electrophilic group will yield a thermodynamic relationship favorable to breaking of the bond between the electrophilic group and the inhibitor moiety. However, it is within the skill of the art to select appropriate combinations taking the above energy relationships into account.

Representative Nu groups contain electron rich oxygen, sulfur and nitrogen atoms. Representative. E groups contain electron deficient carbonyl, thiocarbonyl, phosphonyl and thiophosphonyl moieties. Other useful Nu and E groups will be apparent to those skilled in the art.

In the following listings of representative Nu and E groups, the groups are oriented so that the lefthand bond of Nu is joined to COUP and the righthand bond of Nu is joined to X, while the lefthand bond of E is joined to X and the righthand bond of E is joined to INH.

Representative Nu groups include:

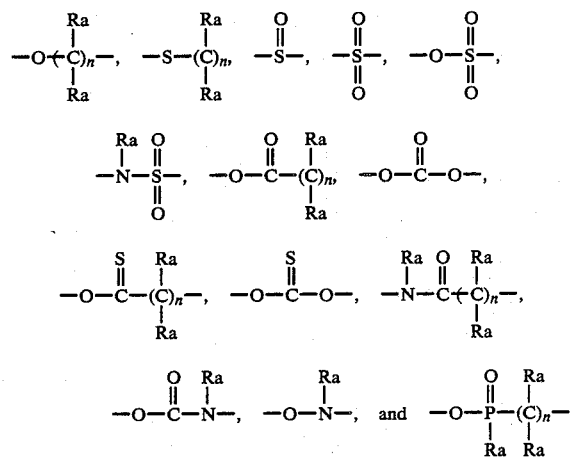

where each Ra is independently hydrogen, alkyl, such as alkyl of 1 to 20 carbon atoms including substituted alkyl such as methyl, ethyl, propyl, hexyl, decyl, pentadecyl, octadecyl, carboxyethyl, hydroxypropyl, sulfonamidobutyl and the like, or aryl, such as aryl of 6 to 20 carbon atoms including substituted aryl such as phenyl, naphthyl, benzyl, tolyl, t-butylphenyl, carboxyphenyl, chlorophenyl, hydroxyphenyl and the like, and n is an integer from 0 to 4 such that the ring Formed by Nu, X and E upon nucleophilic attack of Nu upon the electrophilic center in E contains 3 to 7 ring atoms. Preferably Ra is hydrogen, alkyl of 1 to 4 carbon atoms or aryl of 6 to 10 carbon atoms.

Representative E groups include:

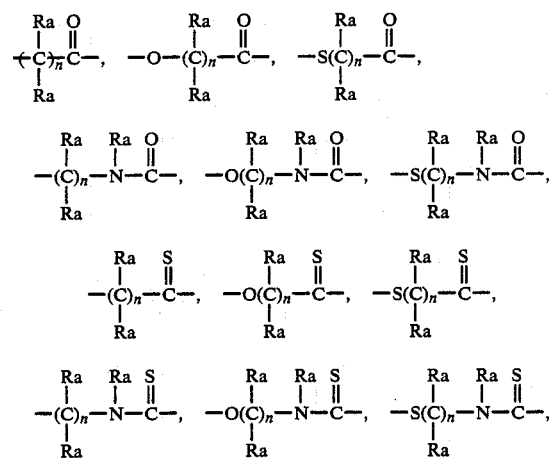

-continued

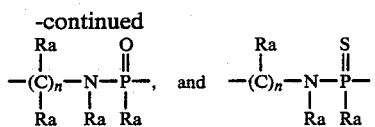

where Ra and n are as defined above.

E is preferably an electrophilic group selected from the group consisting of

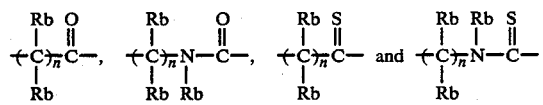

wherein each Rb is independently hydrogen, alkyl, such as alkyl containing 1 to 20 carbon atoms, preferably alkyl containing 1 to 4 carbon atoms, or aryl, such as aryl containing 6 to 20 carbon atoms, preferably aryl containing 6 to 10 carbon atoms; and n is 0 to 4, such that the ring formed upon reaction of the nucleophilic center in Nu with the electrophilic center in E contains 5- or 6-members.

The linking group represented by X can be an acyclic group such as alkylene, for example methylene, ethylene or propylene, or a cyclic group such as an aromatic group, such as phenylene or naphthylene, or a heterocyclic group, such as furan, thiophene, pyridine, quinoline or benzoxazine. Preferably X is alkylene or arylene. The groups Nu and E are attached to X to provide, upon release of Nu From COUP, favorable spatial relationship for nucleophilic attack of the nucleophilic center in Nu on the electrophilic center in E. When X is a cyclic group, Nu and E can be attached to the same or adjacent rings. Aromatic groups in which Nu and E are attached to adjacent ring positions are particularly preFerred X groups.

X can be unsubstituted or substituted. The substituents can be those which will modiFy the rate of reaction, diffusion, or isplacement, such as halogen, including fluoro, chloro, bromo, or iodo, nitro, alkyl of 1 to 20 carbon atoms, acyl, such as carboxy, carboxyalkyl, alkoxycarbonyl, alkoxycarbonamido, sulfoalkyl, alkylsulfonamido, and alkylsulfonyl, solubilizing groups, ballast groups and the like, or they can be substituents which are separately useful in the photographic element such as a stabilizer, an antifoggant, a dye (such as a filter dye or a solubilized masking dye) and the like. For example, solubilizing groups will increase the rate of diffusion; ballast groups will decrease the rate of diffusion; electron withdrawing groups will decrease the rate of displacement of the INH group.

As used herein the term "electron transfer down a conjugated chain" is understood to refer to transfer of an electron along a chain of atoms in which alternate single bonds and double bonds occur. A conjugated chain is understood to have the same meaning as commonly used in organic chemistry. Electron transfer down a conjugated chain is as described in, for example, U.S. Pat. No. 4,409,323.

For convenience herein when the timing group T is of the type described in U.S. Pat. No. 4,409,323, the timing group can be described as a "quinone methide timing group". Examples of useful couplers as described comprising a quinone-methide timing group are as follows:

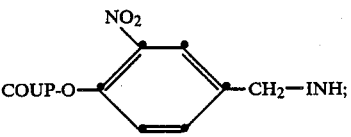

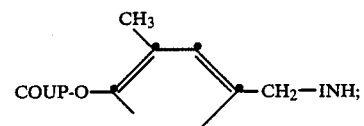

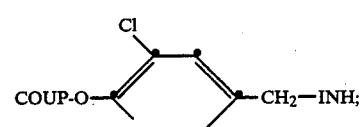

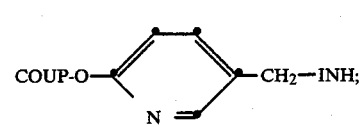

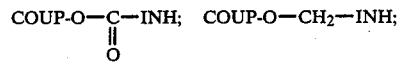

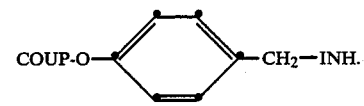

Wherein COUP and INH are as described.

There follows a listing of patents and publications which describe representative useful COUP groups. In these structures Y represents —T—INH—CH$_2$—Q as described. In the case of dye-forming couplers that are useful with a coupler (A), the Y group represents hydrogen or s coupling off group known in the photographic art. The timing group can comprise a single timing moiety or at least two timing moieties, such as described in U.S. Pat. No. 4,698,297 and European Patent Application No. 255,085.

I. COUP's

A. Couplers which form cyan dyes upon reaction with oxidized color developing agents are described in such representative patents and publications as: U.S. Pat. Nos. 2,772,162, 2,895,826, 3,002,836, 3,034,892, 2,474,293, 2,423,730, 2,367,531, 3,041,236 and "Farbkuppler-eine Literaturübersicht, published in Agfa Mitteilungen, Band III, pp. 156–175 (1961).

Preferably such couplers are phenols and naphthols which form cyan dyes on reaction with oxidized color developing agent a:nd have the —Nu—X—E—INH coupling-off group attached at the coupling position, that is the carbon atom in the 4-position. Structures of preferred such coupler moieties are:

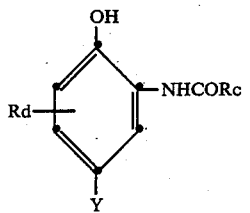

IA-1

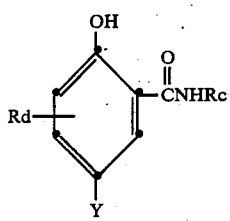

IA-2

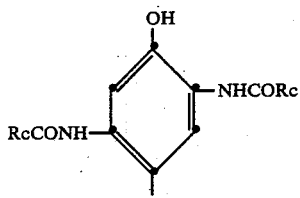

IA-3

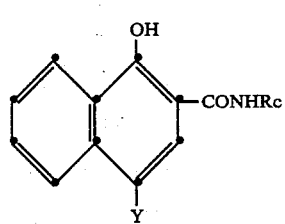

IA-4 where Rc represents a ballast group, and Rd represents one or more halogen such as chloro or fluoro, lower alkyl containing 1 to 4 carbon atoms, such as methyl, ethyl, or butyl; or alkoxy containing 1 to 4 carbon atoms, such as methoxy, ethoxy, or butoxy groups.

B. Couplers which form magenta dyes upon reaction with oxidized color developing agent are described in such representative patents and pubications as: U.S. Pat. Nos. 2,600,788, 2,369,489, 2,343,703, 2,311,082, 3,152,896, 3,519,429, 3,062,653, 2,908,573 and "Farbkuppler-eine Literaturübersicht," published in Agfa Mitteilungen,Band III, pp. 126–156 (1961).

Preferably, such couplers are pyrazolones and pyrazolotriazoles which form magenta dyes upon reaction with oxidized color developing agents and have the Y attached to the coupling position. Structures of preferred such coupler moieties are:

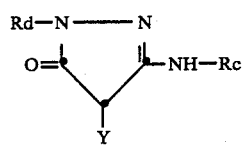

IB-1

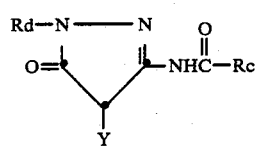

IB-2

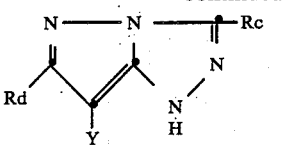

IB-3

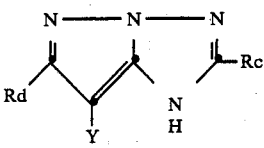

IB-4 where Rc and Rd are chosen independently to be e ballast group, unsubstituted or substituted alkyl, unsubstituted or substituted phenyl.

C. Couplers which form yellow dyes upon reaction with oxidized and color developing agent are described in such representative patents and publications as: U.S. Pat. Nos. 2,875,057, 2,407,210, 3,265,506, 2,298,443, 3,048,194, 3,447,928 and "Farbkuppler-eine Literaturü bersicht," published in Agfa Mitteilungen, Band III, pp. 112–126 (1961).

Preferably such yellow dye forming couplers are acylacetamides, such as benzoylacetanilidesnd have the Y group attached to the coupling position, that is the active methylene carbon atom.

Structures of preferred such coupler moieties are:

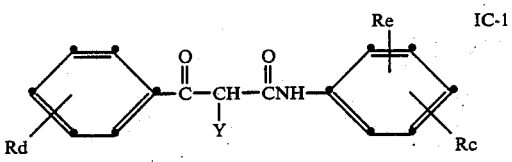

IC-1

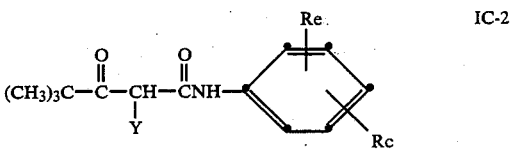

IC-2 where Rc is as defined above and Rd and Re are hydrogen or one or more halogen, alkyl containing 1 to 4 carbon atoms, such as methyl and ethyl, or ballast groups, such as alkoxy of 16 to 20 carbon atoms.

D. Couplers which form colorless products upon reaction with oxidized color developing agent are described in such representative patents as: U.K. Pat. No. 861,138; U.S. Pat. Nos. 3,632,345, 3,928,041, 3,958,993 and 3,961,959. Preferably such couplers are cyclic carbonyl containing compounds which form colorless products on reaction with oxidized color developing agent and have the Y group attached to the carbon atom in the α-position with respect to the carbonyl group.

Structures of preferred such coupler moieties are:

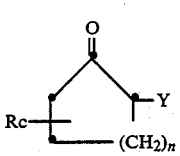

ID-1

-continued

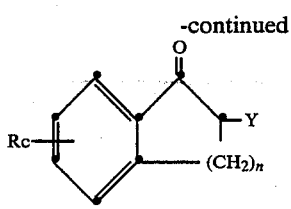
ID-2

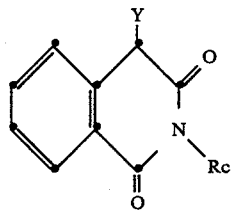
ID-3

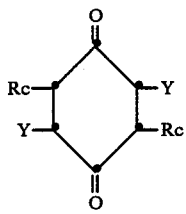
ID-4 where Rc is as defined above and n is 1 or 2.

E. Couplers which form black dyes upon reaction with oxidized color developing agent are described in such representative patents as U.S Pat. Nos. 1,939,231; 2,181,944; 2,333,106; and 4,126,461; German OLS Nos. 2,644,194 and 2,650,764.

Preferably such couplers are resorcinols or m-aminophenols which form black or neutral products on reaction with oxidized color developing agent and have the Y group para to a hydroxy group.

Structures of preferred such coupler moieties are:

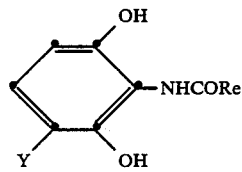
IE-1

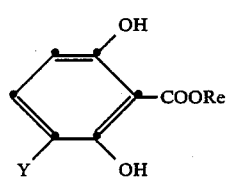
IE-2

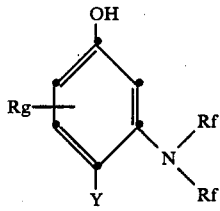
IE-3 where Re is alkyl of 3 to 20 carbon atoms, phenyl or phenyl substituted with hydroxy, halo, amino, alkyl of 1 to 20 carbon atoms or alkoxy of 1 to 20 carbon atoms; each Rf is independently hydrogen, alkyl of 1 to 20 carbon atoms, alkenyl of 1 to 20 carbon atoms, or aryl of 6 to 20 carbon atoms; and Rg is one or more halogen, alkyl of 1 to 20 carbon atoms, alkoxy of 1 to 20 carbon atoms or other monovalent organic groups.

Other useful compounds in such photographic elements include, for example,

F. Compounds that can release hydrazide moieties, such as described in U.S. Pat. Nos. 4,684,604; and G. Compounds that can release a developer, such as described in U.S. Pat. Nos. 3,379,529 and 3,639,417.

Examples of timing groups that enable an intramolecular nucleophilic displacement reaction are as follows:

A. Acyclic groups:

IIA-1 wheren is 1–4, preferably 2 or 3, $Z_1$ is

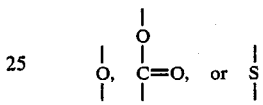

and $R_3$ is hydrogen, alkyl, such as alkyl of 1 to 20 carbon atoms, preferably alkyl or 1 to 4 carbon atoms, or aryl, such as aryl of 6 to 20 carbon atoms, preferably aryl of 6 to 10 carbon atoms.

B. Aromatic groups:

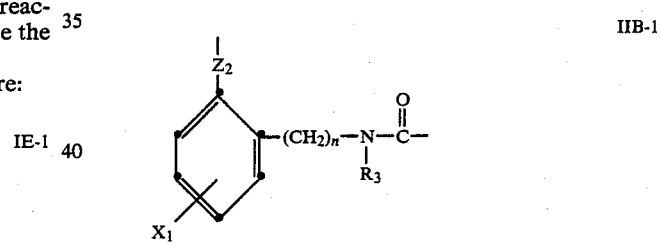
IIB-1

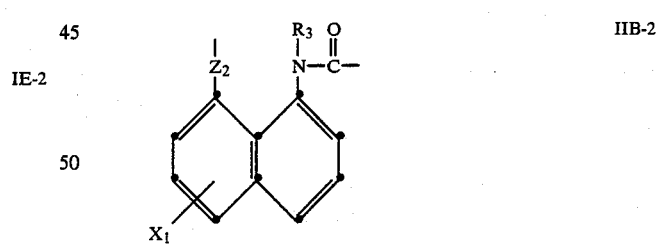
IIB-2 where n is 0 or 1; $Z_2$ is

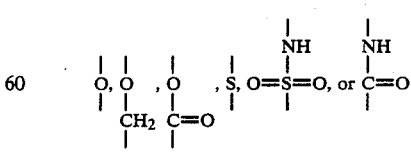

$R_3$ is hydrogen, alkyl, such as alkyl containing 1 to 30 carbon atoms, or aryl, such as phenyl and naphthyl; and $X_1$ is hydrogen or one or more substituent groups independently selected from cyano, fluoro, chloro, bromo, iodo, nitro, alkyl, such as alkyl of 1 to 20 carbon atoms, a dye, —OR$_4$, —COOR$_4$, —CONHR$_4$, —NHCOR$_4$, NHSO$_2$R$_4$, —SO$_2$NHR$_4$ of SO$_2$R$_4$, where R$_4$ is hydrogen, alkyl, such as alkyl of 1 to 20 carbon atoms, preferably alkyl of 1 to 4 carbon atoms, or aryl, such as aryl of 6 to 20 carbon atoms, preferably aryl of 6 to 10 carbon atoms.

C. Heterocyclic groups:

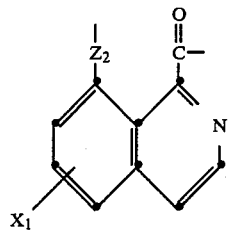

IIC-1

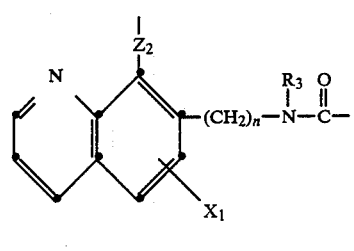

IIC-2

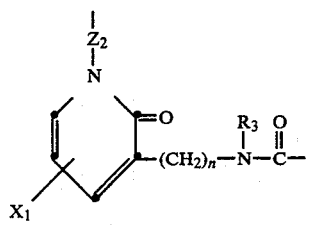

IIC-3 where n is 0 or 1, Z$_2$, X$_1$ and R$_3$ are as defined above.

D. Bis groups:

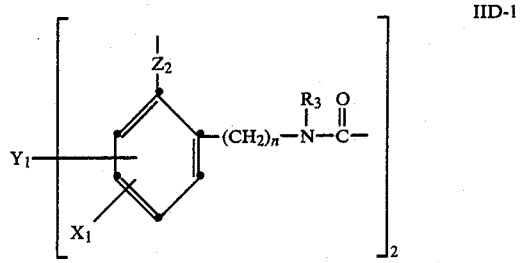

IID-1 where Y$_1$ is a linking group, such as

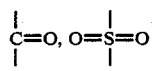

or —NHSO$_2$CH$_2$SO$_2$NH—; n is 0 or 1 and X$_1$, Z$_2$ and R$_3$ are as defined above.

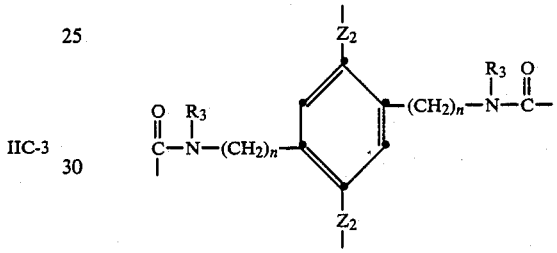

where n is 0 or 1 and Z$_2$, and R$_3$ are as defined above.

Such timing groups are described in, for example, U.S. Pat. No. 4,248.962.

Other useful timing groups, as described include illustrative timing groups described in U.S. Pat. Nos. 4,409,323; 4,684,604; 4,546,073; 4,618,571; 4,698,297; 4,737,451; German OLS No. 3,319,428; and European Patent Application No. 255,085.

Preferred development inhibitor groups (INH) are heterocyclic groups derived from such compounds as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzotriazoles and benzodiazoles.

Typical examples of useful inhibitor groups (INH) are as follows: In each of the structures, R$_1$ is CH$_2$—Q, preferably

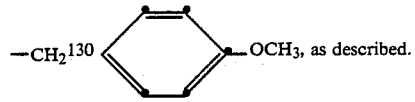, as described.

(A)

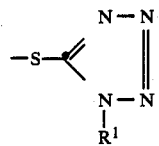

Specific examples are:

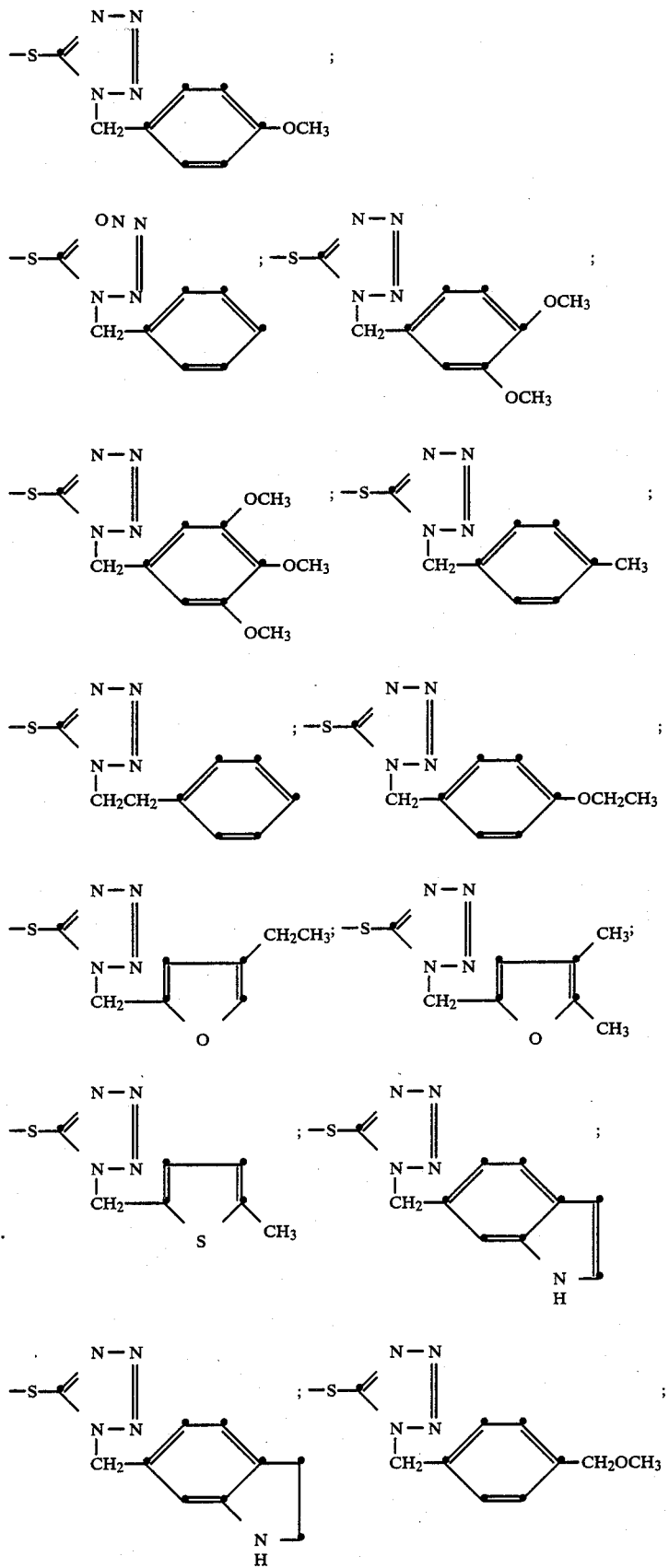

-continued
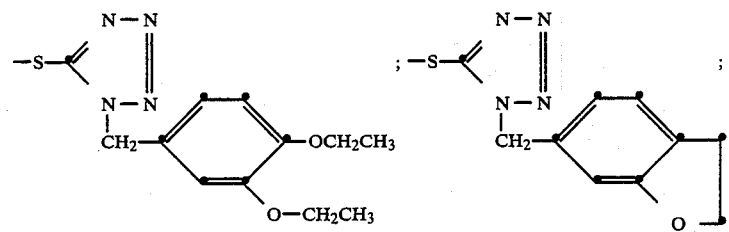
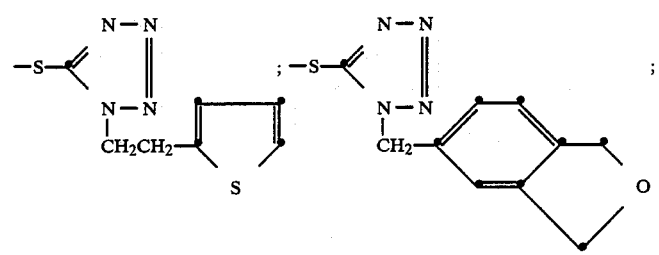
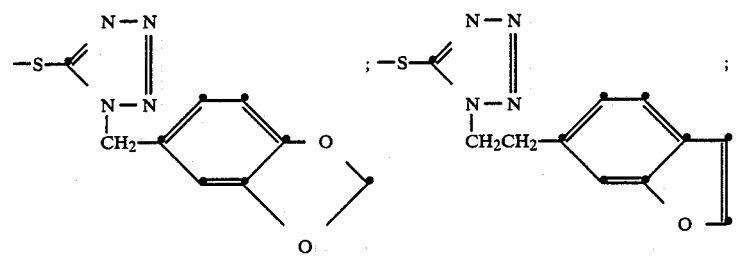
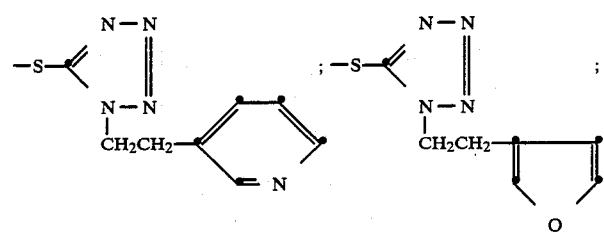
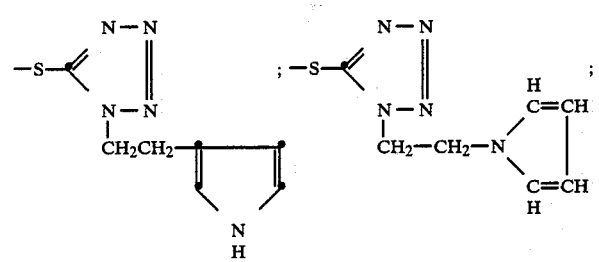
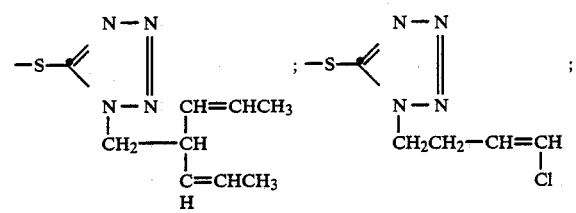
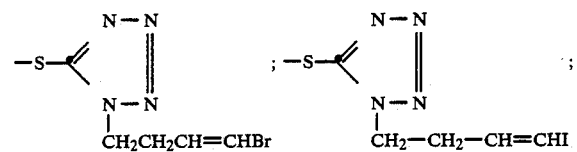

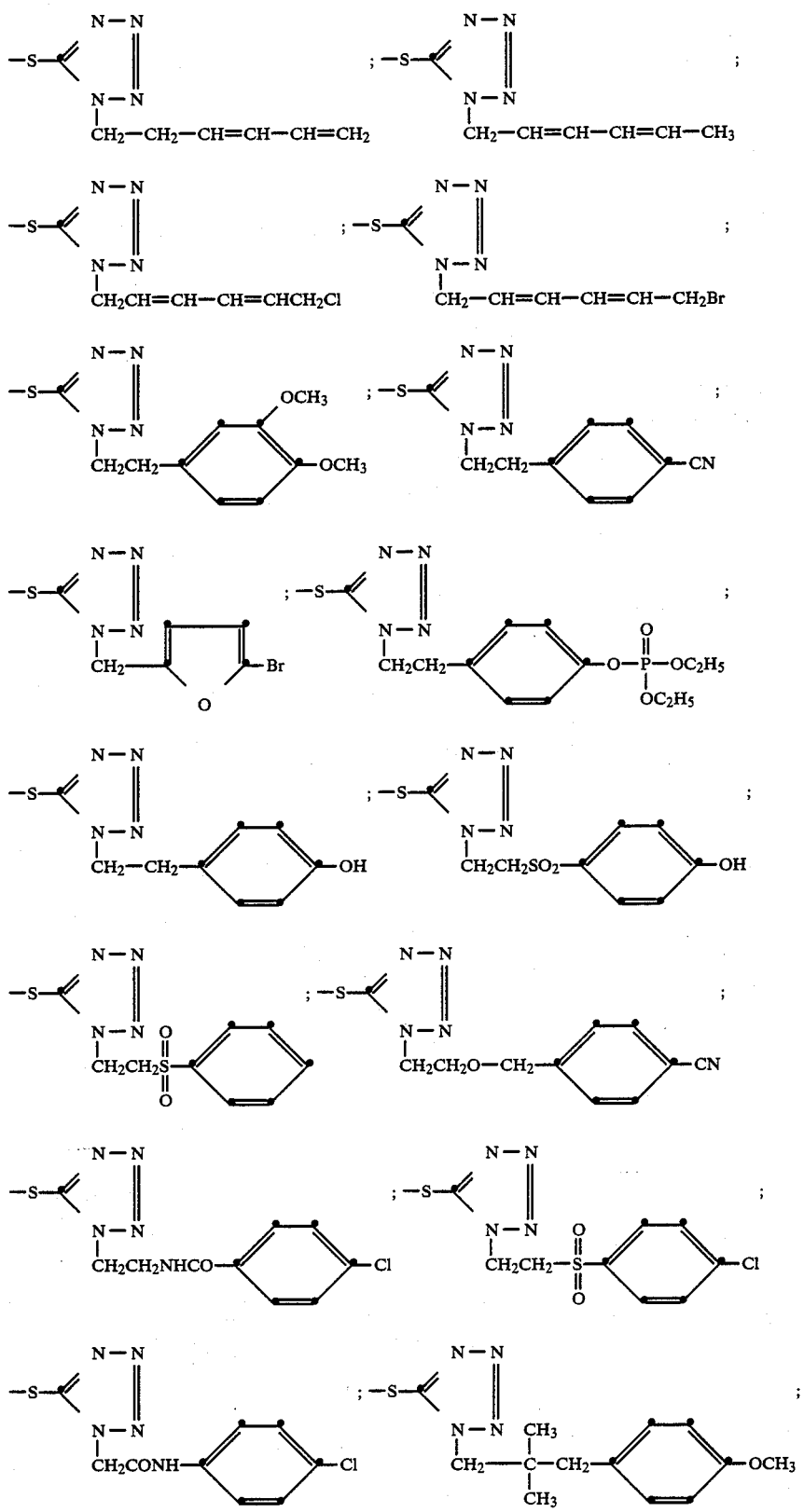

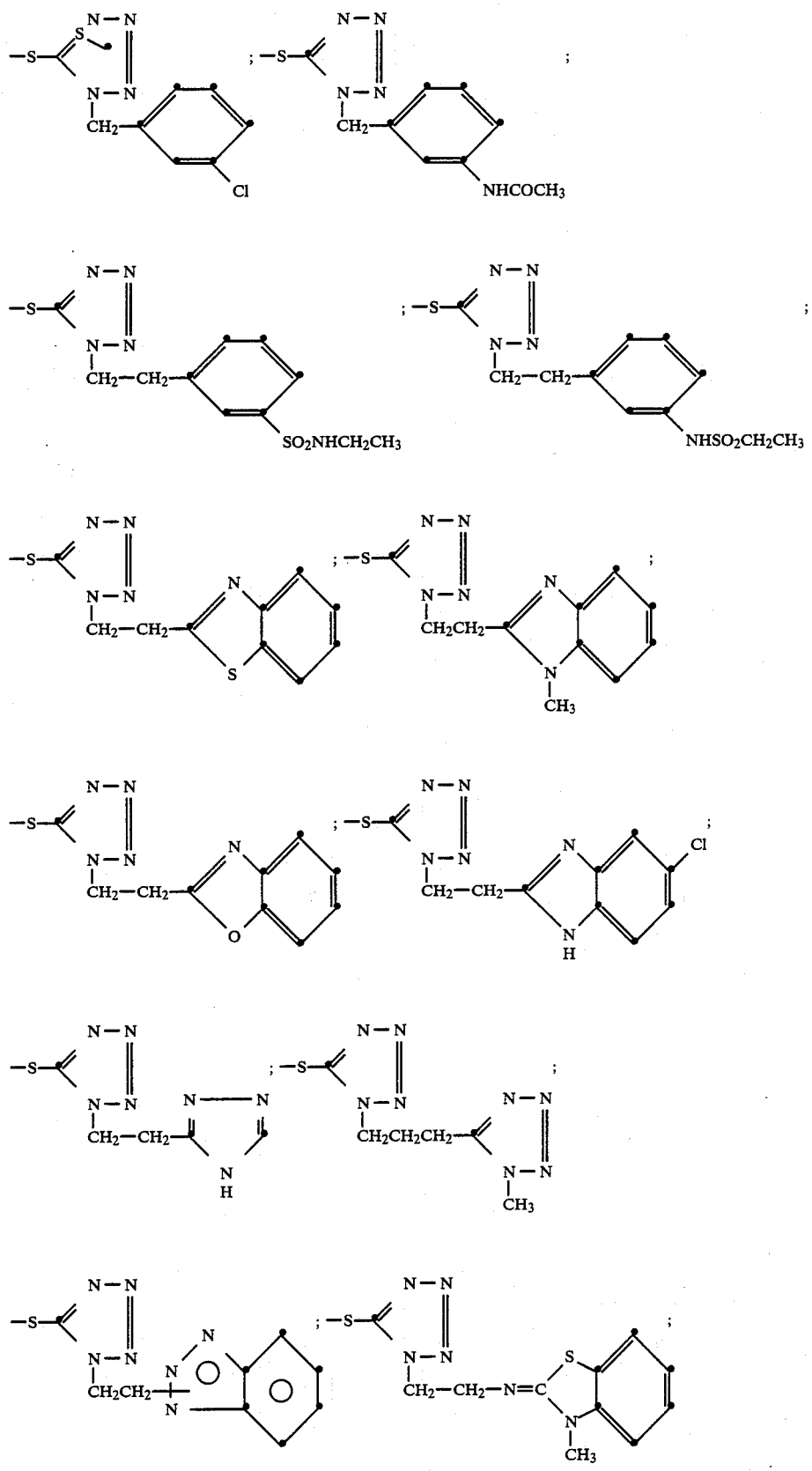

-continued
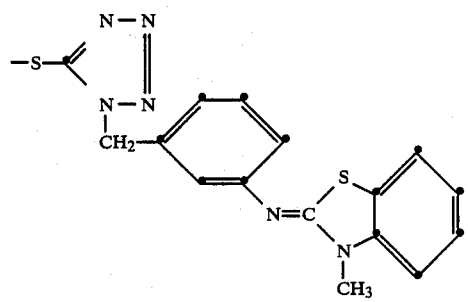
(B) 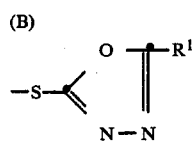
Specific examples are:
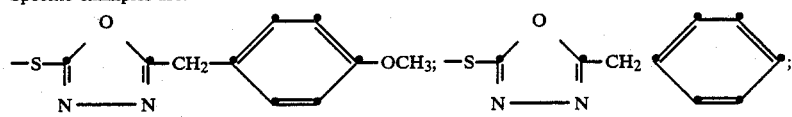
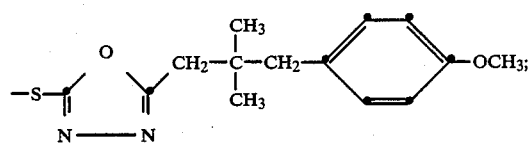
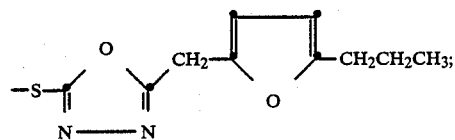
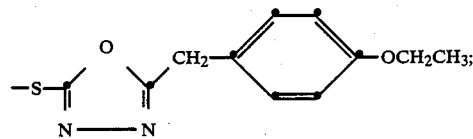
(C) 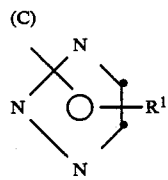
Specific examples are:
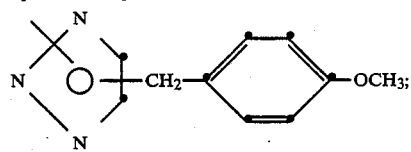
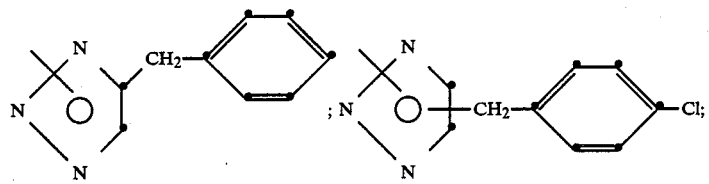

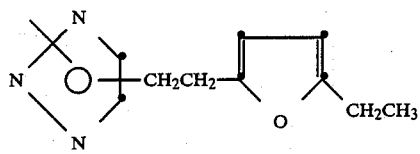
(D)
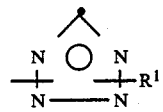
Specific examples are:
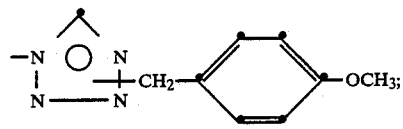
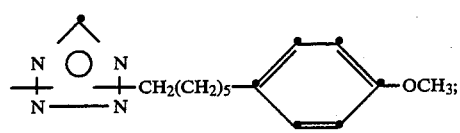
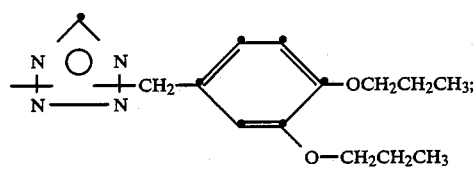
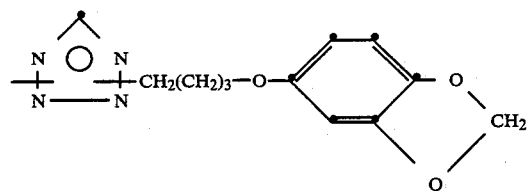
(E)
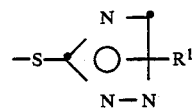
Specific examples are:
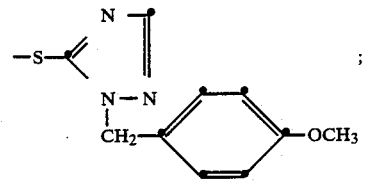
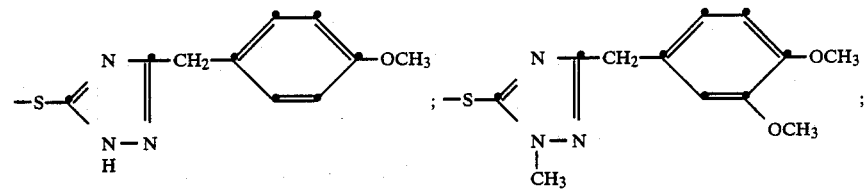

-continued
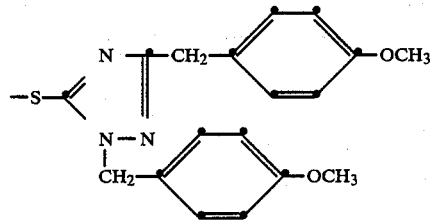
(F)
Specific examples are:
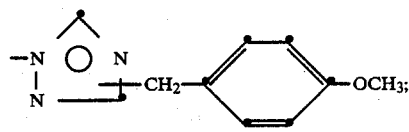
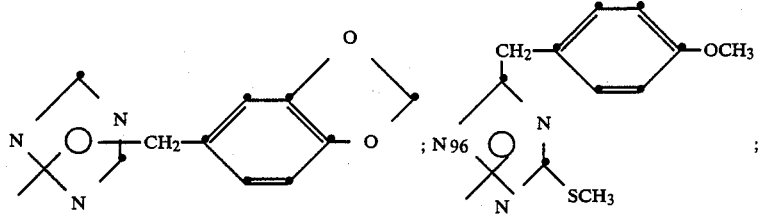
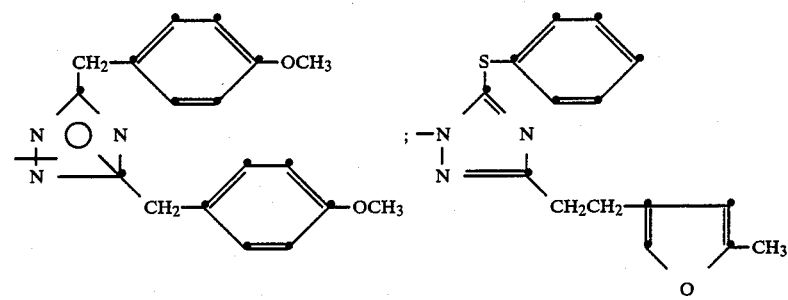
(G)
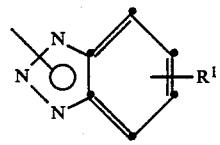
Specific examples are:
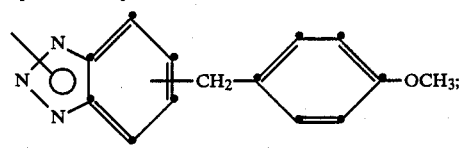

-continued
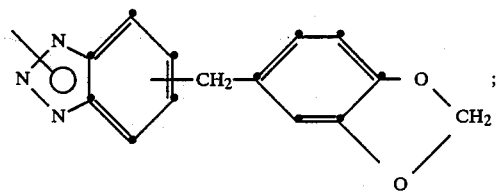
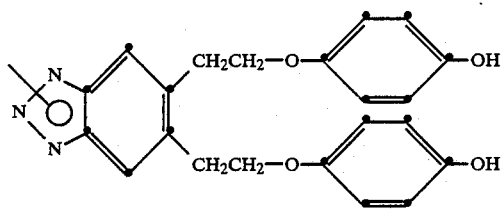
(H)
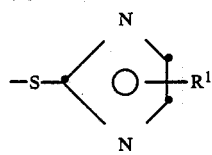
Specific examples are:
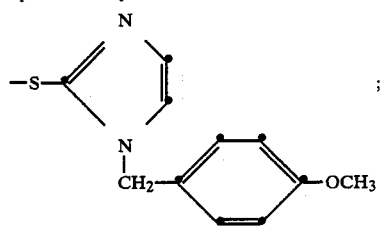
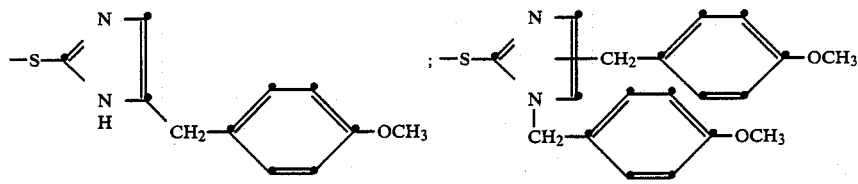
(I)
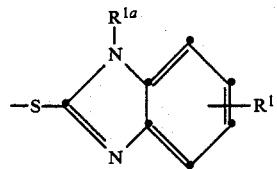
wherein $R^1a$ is hydrogen or an unsubstituted or substituted hydrocarbon group, such as methyl, ethyl, propyl, n-butyl or phenyl.
Specific examples are:
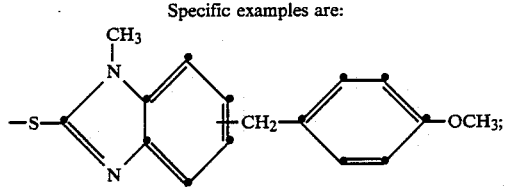

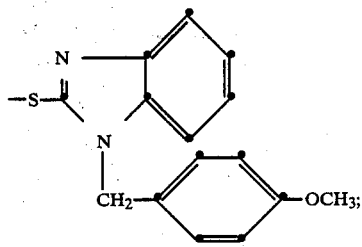
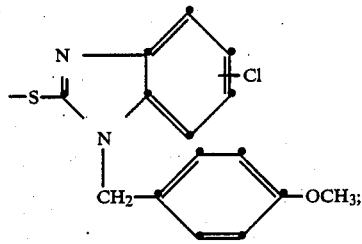
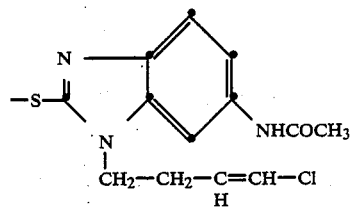
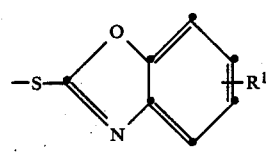
(J)
Specific examples are:
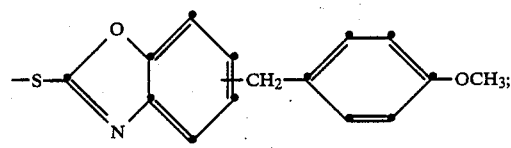
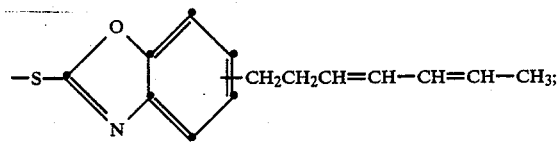
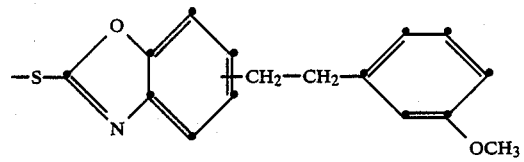
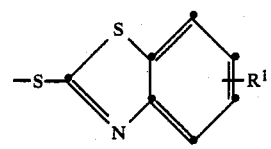
(K)
Specific examples are:

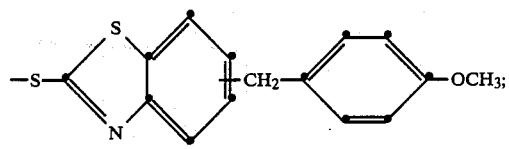
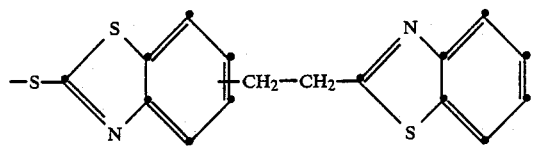
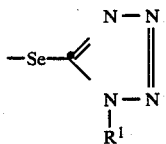
(L)
A Specific example is:
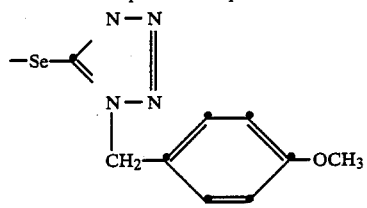
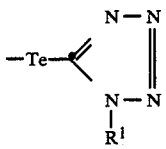
(M)
A Specific example is:
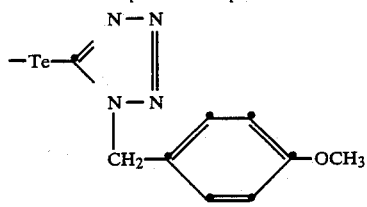
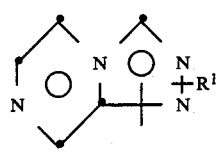
(N)
A specific example is:
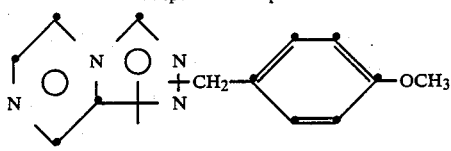
A preferred photographic element, as described, comprises a development inhibitor releasing coupler, also as described, comprising a releasable development inhibitor moiety selected from the group consisting of
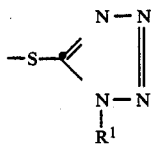

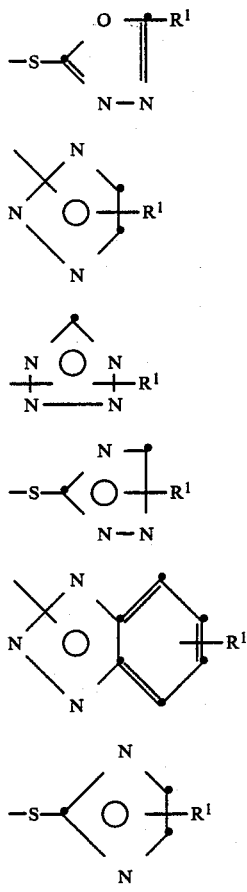

wherein R[1] is

The timing group T and INH are selected and prepared to adjust to the activity of the adjoining coupler moiety, and the other groups of the coupler in order to optimize release of the INH for its intended purpose. Accordingly, INH groups of differing structural types are useful which enable timing groups having a range of activities. Various properties, such as pKa are also usefully considered in optimizing the selection of optimum groups for a particular purpose. An example of such a selection could involve, for instance, a benzotriazole moiety as an inhibitor. Such a benzotriazole moiety can be released too quickly for some intended purposes from a timing group which involves an intramolecular nucleophilic displacement mechanism; however, the benzotriazole moiety can be modified as appropriate by substituent groups that change the rate of release.

The photographic coupler as described can be incorporated in photographic elements and/or in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements as described can be processed by conventional techniques in which color forming couplers and color developing agents are incorporated in separate processing solutions or compositions or in the element.

Photographic elements in which the coupler (A) is incorporated can be a simple element comprising a support and a single silver halide emulsion layer or they can be multilayer, multicolor elements. The coupler (A) can be incorporated in at least one of the silver halide emulsion layers and/or in at least one other layer, such as an adjacent layer, where it will come into reactive association with oxidized color developing agent which has developed silver halide in the emulsion layer. The silver halide emulsion layer can contain or have associated with it, other couplers, such as dye forming couplers, colored masking couplers, and/or competing couplers. These other photographic couplers can form dyes of the same or different color and hue as the photographic couplers of this invention. Additionally, the silver halide emulsion layers and other layer of the photographic element can contain addenda conventionally contained in such layers.

A typical multilayer, multicolor photographic element as described can comprise a support having thereon a red sensitive silver halide emulsion unit having associated therewith a cyan dye image providing material, a green-sensitive silver halide emulsion unit having associated therewith a magenta dye image providing material and a blue-sensitive silver halide emulsion unit having associated therewith a yellow dye image-providing material, at least one of the silver halide emulsion units having associated therewith coupler (A) as described. Each silver halide emulsion unit can be composed of one or more layers and the various units and layers can be arranged in different locations with respect to one another.

If COUP, T and/or INH are diffusible moieties, the layer or unit affected by INH can be controlled by incorporating in appropriate locations in the element a scavenger layer which will confine the action of COUP, T and/or INH to the desired layer or unit. At least one of the layers of the photographic element can be, for example, a mordant layer or a barrier layer.

Combinations of development inhibitor releasing couplers are also useful in photographic elements as described. The combinations of such couplers can be combinations of couplers within the scope of the invention as well as combinations of such couplers that release inhibitors known in the photographic art.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

The coupler (A) can be used in photographic elements in the same way as photographic couplers which release inhibitors have previously been used in photographic elements.

Depending upon the nature of the particular INH, the coupler (A) can be incorporated in a photographic element for different purposes and in different locations.

The range of operation between layers of the development inhibitor released from the coupler as described can be controlled by the use of scavenger layers, such as a layer of fine grain silver halide emulsion. Scavenger layers can be in various locations in an element containing couplers as described. They can be located between layers, between the layers and the support, or over all of the layers.

Couplers as described can be prepared by method known in the organic compound synthesis art. Typically, the couplers of this invention are prepared by first attaching the timing group to the appropriate coupler moiety, or a derivative of the coupler moiety. The product is then reacted with an appropriate derivative of the inhibitor to form the desired coupler. Known reactions are employed to perform these steps. The following examples illustrate the way in which these steps can be performed using specific reactants and reactions.

The following compounds illustrate methods of preparing compounds according to the invention.

SYNTHESIS EXAMPLE A—PREPARATION OF COMPOUND 2

A. Preparation of 1-(p-Methoxybenzyl)tetrazoline-5-thione (S-4), also named as methoxybenzylmercaptotetrazole.

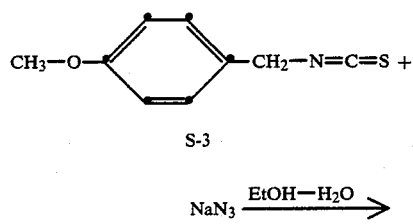

S-3

$$NaN_3 \xrightarrow{EtOH-H_2O}$$

-continued

S-4

To a mechanically stirred slurry of 112 g (0.625 mole) 4 methoxylbenzylisothiocyanate (S-3) in 800 ml ethanol under a nitrogen atmosphere was added in a slow stream 81.3 g (1.25 mole) sodium azide dissolved in 400 ml water. The resulting reaction mixture was refluxed for 16 hours, cooled to room temperature (20° C.) and filtered. The filtrate was extracted twice with ether, and then acidified to pH=1 with concentrated hydrochloric acid. The resulting precipitate was filtered off and recrystallized from ethyl acetate hexane to yield 20 g of a white solid S-4 m.p. 162°-4° C.

B. PREPARATION OF CARBAMOYL CHLORIDE INTERMEDIATE S-6

S-5

$$\xrightarrow{1. \; N(C_2H_5)_3}{COCl_2, DMA}$$

S-6

A slurry of S-5 amine hydrochloride (38.8 g, 0.054 mole) and triethylamine (5.45 g, 0.054 mole) in 300 ml dry tetrahydrofuran was stirred at room temperature (20° C.) under a nitrogen atmosphere for one hour and then filtered, N,N-dimethylaniline (9.1 g, 0.075 mole) was added to the filtrate and the resulting mixture added dropwise to 100 ml of a stirred 12% phosgene in toluene solution. The reaction was cooled in an ice-acetone bath under a nitrogen atmosphere.

After one hour, the reaction mixture was filtered and the filtrate concentrated in vacuo and the resulting gum (S-6) used directly in the next reaction.

C. Preparation of Compound 2

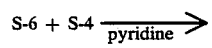

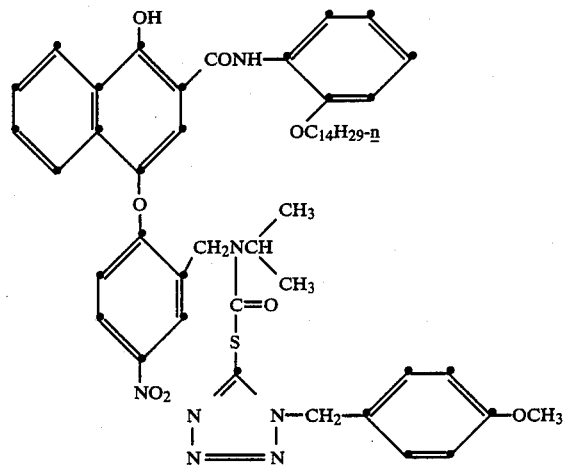

To a room temperature solution of carbamoyl chloride (S-6) (≃0.054 mole from Previous reaction) in 250 ml pyridine was added in one portion 12 g (0.054 mole) of 4 methoxybenzylmercaptotetrazole (S-4) and the resulting solution stirred for fifteen hours under a nitrogen atmosphere.

The reaction mixture was then quenched in ca. 1.5 l ice water mixture containing 250 ml concentrated hydrochloric acid. This mixture was extracted with ethyl acetate (3×). The combined extracts were washed with 5% hydrochloric acid (2×), water (2×), brine, dried over anhydrous magnesium sulfate, filtered, and evaporated in vacuo. After chromatography over silica gel (cyclohexane-ethyl acetate)-the product containing fractions were combined, evaporated in vacuo and the resulting gum crystallized from hexane-ethyl acetate to yield 6 g of an off-white solid, m.p. 92°–5° C.

The elemental analysis was correct for Compound 2. Calculated: C, 65.7; H, 6.55; N, 10.5; S, 3.4; Found: C, 65.1; H, 6.50; N, 10.4; S, 3.6.

SYNTHESIS EXAMPLE B—PREPARATION OF COMPOUND 14

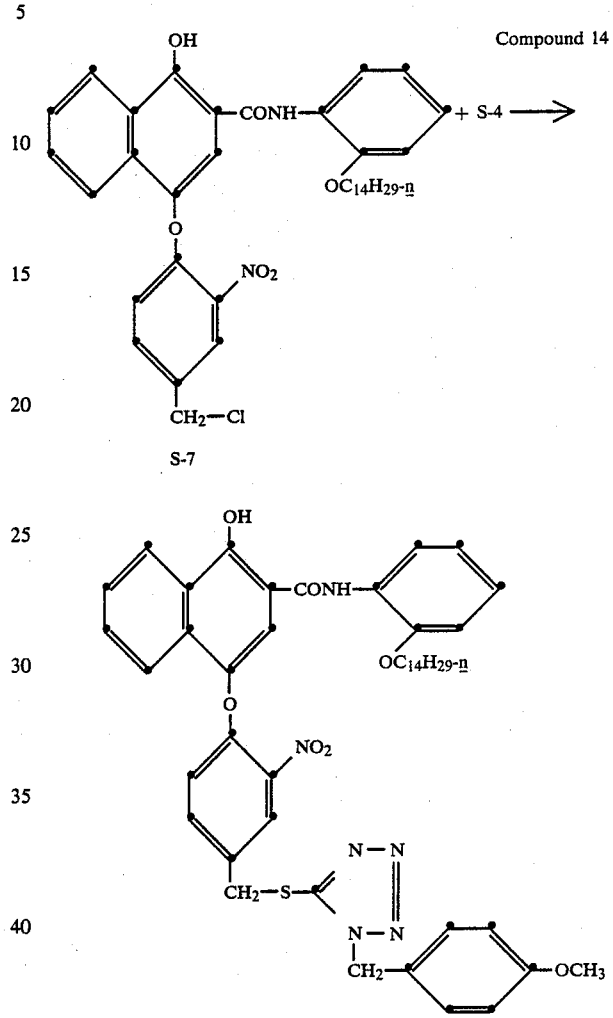

A mixture of 6.6 g (10 mmol) benzyl chloride (S-7), 2.2 g (10 mmole) 4- methoxybenzyl mercaptotetrazole (S-4 ), 0.8 g, 10 mmole) sodium bicarbonate, and 0.05 g tetrabutylammonium bromide in 50 ml dichloromethane and 30 ml water was stirred at room temperature for 18 hours at which time an additional 0.44 g (S-4) and 0.12 g sodium bicarbonate was added. After our more hours, the organic layer was separated, dried over anhydrous magnesium sulfate, filtered, and concentrated in vacuo. The resulting oil was chromatographed over silica (dichloromethane) and the product-containing eluants were combined and concentrated in vacuo to yield an oil which was crystallized From acetic acid to yield 3.0 g of the desired product Compound 14, m.p. 75°–6° C.

The elemental analysis was correct for Compound 14. Calculated: C, 66.6; H, 6.4; N, 9.9; S, 3.8; Found: C, 66.7; H, 6.7; N, 9.9; S, 3.6.

SYNTHESIS EXAMPLE C—PREPARATION OF COMPOUND 3

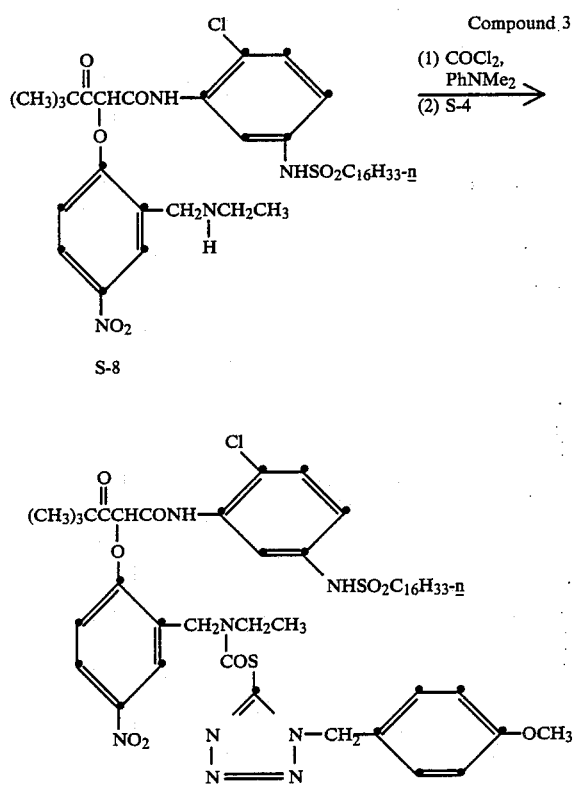

To 39.2 ml of a 12% Phosgene in toluene solution under a nitrogen atmosphere and cooled to 0° C. was added dropwise with stirring a solution of 14.7 g S-8 amine (19 6 mmol) and 3.7 ml (29.4 mmol) N,N dimethylaniline in 40 ml dry tetrahydrofuran. After 2 hours at room temperature. The mixture was concentrated in vacuo and the residue dissolved in 40 ml pyridine, 4 methoxybenzylmercaptotetrazole (S-4) (4.6 g, 20.6 mmol) was added in one portion and the mixture stirred at room temperature under nitrogen for 12 hours. The reaction mixture was then diluted with ether, and the ether layer separated and washed with 10% hydrochloric acid, 5% aqueous sodium bicarbonate solution, brine, dried over anhydrous magnesium sulfate, filtered, and concentrated in vacuo to give a yellow oil. After chromatography over silica gel (ethyl acetate-cyclohexane), the product containing eluants were combined and concentrated in vacuo to give 2.0 g Compound 3 as an off-white solid, m.p. 67°-9° C.

The structure was confirmed by n.m.r., infrared, and mass spectra, as well as an elemental analysis: Calculated: C, 57.7; H, 6.8; N, 11.2; S, 6.4; Found: C, 57.5; H, 6.8; N, 11.3; S, 6.7.

SYNTHESIS EXAMPLE D—PREPARATION OF 2-(P-METHOXYBENZYL) 5-MERCAPTO-OXADIAZOLE

A. Preparation of p-methoxyphenylacetylhydrazide

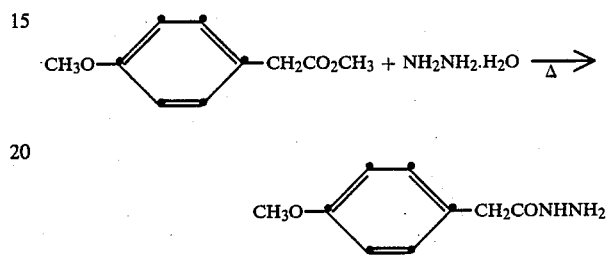

A suspension of 100 g (0.55 mole) methyl-4-methoxyphenylacetate in 200 ml of hydrazine monohydrate was refluxed until a homogeneous solution resulted. After cooling to room temperature, the resulting crystals were filtered, and recrystallized from alcohol to yield 86.8 g of a white solid, m.p. 115°-23° C.

B. Preparation of 2-mercapto-5-(p-methoxybenzyl)oxadiazole

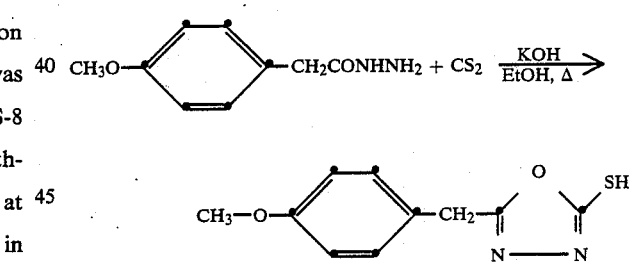

Carbon disulfide (80ml) was added dropwise with stirring at room temperature to a slurry of p-methoxyphenylacetylhydrazide (72 g, 0.4 mole) and potassium hydroxide (22.4 g, 0.4 mole) in 400 ml absolute alcohol. The resulting mixture was refluxed for 14 hours under nitrogen, and the solvent removed in vacuo. The concentrate was taken up in water, acidified with hydrochloric acid, and extracted with ether. The ether extracts were combined, washed with water and brine, dried over magnesium sulfate, filtered, and then concentrated to yield a solid which was crystallized from aqueous alcohol to yield 29.7 g of a white solid, m.p. 90°-92° C.

C Preparation of Compound 51

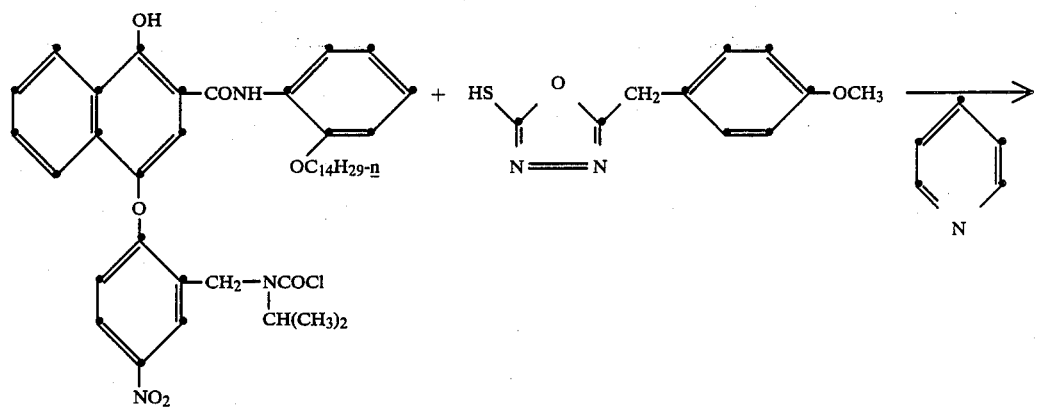

Compound 51

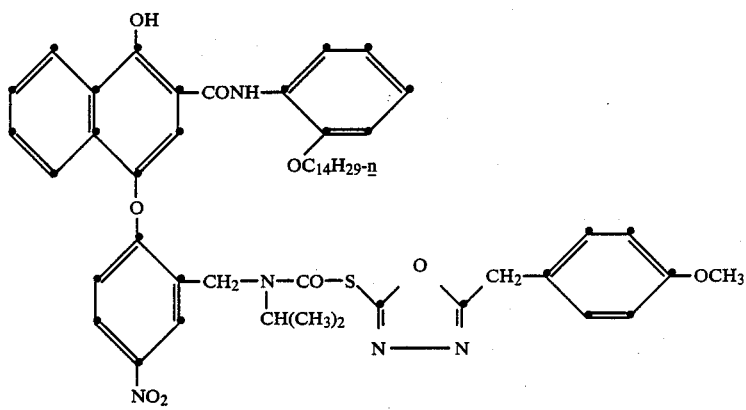

35

A solution of the above carbamoyl chloride (22.3 g, 0.03 mole) and 2-mercapto-5-(p-methoxybenzyl)oxadiazole (6.66 g) 0.03) in 200 ml pyridine was stirred under nitrogen at room temperature for fifteen hours. The reaction mixture was poured into 1.5 l ice-water mixture containing 200 ml concentrated hydrochloric acid and extracted with ethyl acetate. The combined extracts were washed with 5% hydrochloric acid, 5% aqueous sodium carbonate, and brine. After drying over anhydrous magnesium sulfate, the extracts were filtered, concentrated in vacuo, and the resulting gum chromatographed over silica gel (methylene chloride). The product containing fractions were combined, evaporated in vacuo, and the resulting solid crystallized from hexane-ethyl acetate to yield 13 g of the desired product as a white solid, m.p. 72°–5° C.

The elemental analysis was correct for Compound 51: Calculated: C, 66.6; H 6.7; N 7.6; S 3.5 Found: C, 65.9; H 6.6; N 7.0; S 5.5.

SYNTHESIS EXAMPLE E—PREPARATION OF COMPOUND 13

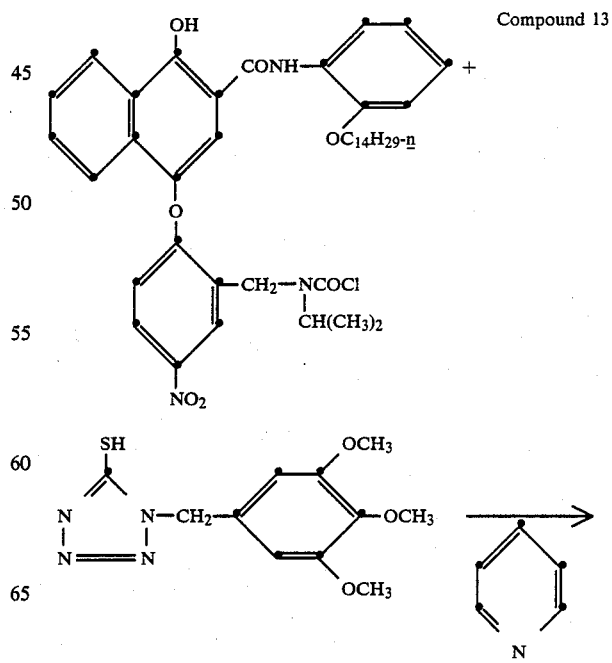

Compound 13

-continued

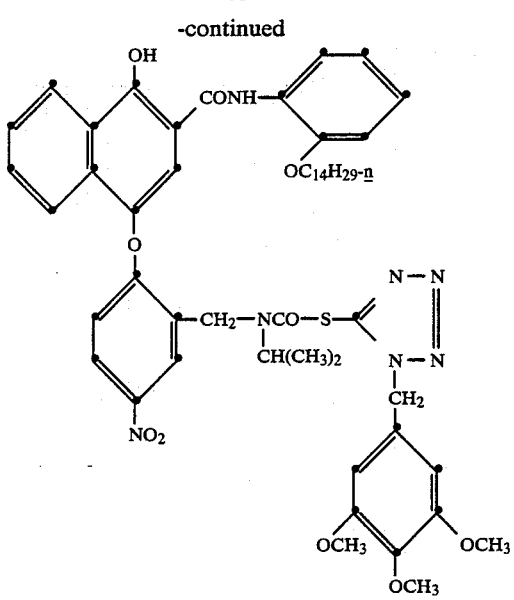

A solution of the above carbamoyl chloride (29.0 g, 0.04 mole) and 3,4,5 trimethoxybenzylmercaptotetrazole (11.3 g, 0.04 mole) in 200 ml pyridine was stirred under nitrogen at room temperature for fifteen hours. The reaction mixture was poured into ca. 1.5 l ice water mixture containing 200 ml concentrated hydrochloric acid and extracted with ethyl acetate. The combined extracts were washed with dilute hydrochloric acid, 5% aqueous sodium carbonate, and brine. After drying over magnesium sulfate, the extracts were filtered, concentrated in vacuo, and the resulting solid chromatographed over silica (heptane-ethyl acetate . The product containing fractions were combined, evaporated in vacuo, and the resulting gum crystallized from alcohol to yield 3.6 g of a white crystalline material, m.p. 87°-9° C.

The elemental analysis was correct for Compound 13: Calculated: C 64.2; H 6.6; N 9.9; S 3.2; Found: C 64.1; H 6.5; N 9.7; S 3.3.

In the following discussion of materials for use in the emulsions and elements of this invention, reference will be made to Research Disclosure. December 1978, Item 14643, published by Industrial Opportunities Ltd., Homewell Havant, Hampshire, P09 1EF, U.K., the disclosures of which are incorporated herein by reference. This publication will be identified hereafter by the term "Research Disclosure".

The silver halide emulsions employed in the elements of this invention can be either negative-working or positive working. Examples of emulsions and their preparation are described in Research Disclosure Sections I and II and the publications cited therein. Tabular photographic silver halide grains are also useful. Examples of useful vehicles for the emulsion layers and other layers of elements of this invention are described in Research Disclosure Section IX and the Publications cited therein.

Described couplers can be incorporated in the elements and emulsions as described in Research Disclosure Section VII, Paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), matting agents (see Research Disclosure Section XVI) and development modifiers (see Research Disclosure Section XXI).

The Photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are
4-amino-3-methyl-N,N-diethylaniline hydrochloride,
4-amino-3-methyl-N-ethyl-N-$\beta$-(methanesulfonamido) ethylaniline sulfate hydrate,
4-amino-3-methyl-N-ethyl-N-$\beta$-hydroxyethylaniline sulfate,
4-amino-3-$\beta$-(methanesulfonamido)ethyl-N,N-diethylaniline hydrochloride and
4-amino-N-ethyl-N-(2-methoxyethyl)-m-toluidine di-p-toluenesulfonic acid.

With negative working silver halide a negative image can be formed. Optionally positive (or reversal) image can be formed.

Development is Followed by the conventional steps of bleaching, fixing, or bleach fixing, to remove silver and silver halide, washing and drying.

The following examples further illustrate the invention.

EXAMPLE 1

PHOTOGRAPHIC EXAMPLE: SHARPNESS AND INTERIMAGE EFFECTS

Thirteen color photographic materials (entries 1-13 in the Table) were Prepared according to the following schematic layer structure (numerical values denote coating coverages in mg/m$^2$):

| Overcoat: | Gelatin - 2500; Gelatin Hardener [bis(vinylsulfonyl)methane] 1.75% |
|---|---|
| Photographic Layer 1: | Green-Sensitive AgIBr - 1600; Gelatin - 2400; Cyan dye forming coupler (IC-1) - 750; +/− DIR compounds (see Table). |
| Interlayer: | Antistain agent 2,5-didodecylhydroquinone - 115 Gelatin - 620. |
| Photographic Layer 2: | Red - Sensitive AgIBr - 1600; Gelatin - 2400;Yellow dye forming coupler (IC-2) - 1300. |
| Film Support | With antihalation gray silver - 324; Gelatin - 2452; Antistain agent - 15. |

Three additional color photographic materials wer prepared (entries 14–16 in the Table) that differed from the first nineteen only in that Yellow dye forming coupler (IC-2) replaced Cyan dye forming coupler (IC-1) in photographic layer 1 and in that Magenta dye forming coupler (IC-3) replaced Yellow dye forming coupler (IC-2) in photographic layer 2.

The dye forming couplers IC-1 and IC-2 were each dispersed in half their weight of di-n-butyl phthalate, the dye forming coupler IC-3 was dispersed in half it's weight of tri-cresyl phosphate and the DIR compounds were each dispersed in twice their weight of diethyl lauramide.

For DIR coupler effect, the samples were exposed through a graduated density test object and a Wratten 99 (green) filter. This exposed photographic layer 1.

For interimage evaluation, the samples were exposed through a graduated density test object and Wratten 12 (minus blue) filter. This exposes both the sensitized photographic layers.

For sharpness, evaluated by calculating CMT acutance values for 16 mm film or by calculating AMT acutance values for a 35 mm film system (this technique is described in an article entitled: "An improved Objective Method for Rating Picture Sharpness: CMT Acutance," by R. G. Gendron, Journal of the SMPTE, 82, 1009-12, 1973), exposures were made through a Wratten 99 (green) filter. Calculations employed the following formulas in which the cascaded area under the system modulation transfer curve is shown in equation (21.104) on p. 629 of The Theory of the Photographic Process, 4th Edition, 1977, edited by T. H. James:

$$CMT = 100 + 42 \log [cascaded\ area/5.4782M]$$

$$AMT = 100 + 66 \log [cascaded\ area/2.6696M']$$

where $M = 11.8$ for 16 mm film and $M' = 3.8$ for 35 mm film system.

The materials were then processed at 38° C. as follows:
Color Developer 2 ¾'
Stop (5% Acetic Acid) 2'
Wash 2'
Bleach $K_3Fe(CN)_6$ 2'
Fix 2'
Wash 2'

The color developer composition was:
$K_2SO_3$ 2.0 g/l
4-amino-3-methyl-N-ethyl
beta-hydroxyethylaniline sulfate 3.35"
$K_2CO_3$ 30.0"
KBr 1.25"
KI 0.0006"
adjusted to pH = 10.0

The oxidized color developing agent generated by development of exposed silver reacts with adjacent image dye forming compounds and DIR compounds to form dyes and to release inhibitor (or inhibitor precursor) in photographic layer 1. The development inhibiting effects of the inhibitor released from the DIR compound were assessed by monitoring the gamma of photographic layer 1. The sharpness effects of the inhibitor released from the DIR compound were assessed by monitoring the acutance of photographic layer 1. Higher values of the acutance indicate greater sharpness in the film.

The interimage effects of the inhibitor released from the DIR compound were assessed by monitoring the ratio of the gammas of photographic layer 1 (causer of interimage) and photographic layer 2 (receiver of interimage). The larger the gamma ratio, the larger the interimage effect (the degree of color correction) in the film.

The table shows the identity of the DIR compound coated, the quantity of that DIR compound (in $mg/m^2$), the gamma of photographic layer 1 (the causer layer), the acutance of photographic layer 1, and the degree of interimage effect (color correction) of photographic layer 1 onto photographic layer 2 (causer gamma/receiver gamma).

DIR compounds A through G are known in the prior art. Table entries 1 through 13 illustrate that the DIR compounds of the invention (characterized by the combination in one DIR compound of a sterically unhindered Q group moiety and an inhibitor core moiety and a timing group moiety) cause adequate degrees of intralayer development suppression and cause greater acutance and lower interimage effects than do DIR compounds of the prior art.

Coatings 2 through 5, which incorporated DIR couplers A through D, illustrate that although variation in the ballast group moiety can alter the interimage behavior observed in the photographic elements, the acutance is not altered. Coatings 6 through 8, which incorporate DIR compounds E through G, illustrate that the use of a timing group moiety in combination with an inhibitor group moiety and typical ballast group moieties can increase the acutance of the photographic element but that the degree of interimage effect also increases. Typically, the higher the degree of interimage effect, the higher the acutance. Coating 9 (which incorporates compound 2 of the invention) illustrates the surprising finding that combination of a timing group moiety with an inhibitor group moiety and a sterically unhindered Q moiety provides DIR compounds which can be incorporated into photographic elements to provide both increased levels of acutance and decreased levels of interimage effect.

Coatings 10 through 13, each of which incorporates a DIR compound of the invention, illustrate that the surprisingly increased acutance and decreased interimage can be achieved with DIR compounds which incorporate a variety of sterically unhindered Q group moieties and with DIR compounds which incorporate a variety of inhibitor group moieties.

Coatings 14 through 16 illustrate that the surprisingly increased acutance and decreased interimage can be achieved using DIR compounds of the invention which incorporate a variety of coupler group moieties.

Coatings 17 through 24 were prepared, exposed and evaluated like coatings 1 through 13 described above. In these cases, the acutance was evaluated relative to a 35 mm film system. Again, the higher the acutance value, the sharper the Film. The quantity of the individual DIR compound evaluated which was required &o bring the amma of photographic layer 1 to a value of 0.65 was employed in each case.

The table lists the quantity of DIR compounds required to cause a gamma of 0.65 in the causer layer, the 35 mm System AMT acutance value of that layer (relative to that obtained in a coating incorporating comparison DIR compound E), and the interimage value as the causer gamma divided by &he receiver gamma).

Coatings 17 through 19 use comparison DIR compounds which incorporate a variety of known timing groups. The comparisons shown in this Table illustrate that the DIR compounds of the invention provide photographic elements which show an improved balance of lower interimage effects and higher acutance values than can be achieved using previously known DIR compounds.

TABLE I

| Coating Number | DIR Compound | Quantity (mg/m²) | Gamma "causer" | CMT 16 mm | Gamma "causer" / Gamma "receiver" |
|---|---|---|---|---|---|
| Control 1 | none | — | 1.70 | 92.2 | 1.14 |
| Comparison 2 | A | 36 | 0.57 | 96.2 | 0.77 |
| Comparison 3 | B | 68 | 0.82 | 95.9 | 0.56 |
| Comparison 4 | C | 38 | 0.61 | 96.2 | 0.52 |
| Comparison 5 | D | 28 | 0.67 | 96.1 | 0.42 |
| Comparison 6 | E | 68 | 0.57 | 99.9 | 1.40 |
| Comparison 7 | F | 78 | 0.83 | 96.4 | 0.79 |
| Comparison 8 | G | 70 | 0.59 | 98.4 | 0.83 |
| Invention 9 | 2 | 68 | 0.59 | 99.8 | 0.85 |
| Invention 10 | 1 | 66 | 0.57 | 100.9 | 1.00 |
| Invention 11 | 5 | 70 | 0.63 | 96.9 | 0.70 |
| Invention 12 | 13 | 75 | 0.62 | 100.7 | 1.26 |
| Invention 13 | 51 | 71 | 0.64 | 97.5 | 0.61 |
| Control 14 | none | — | 2.02 | 90.4 | 1.13 |
| Comparison 15 | H | 65 | 0.83 | 98.5 | 0.96 |
| Invention 16 | 3 | 65 | 0.67 | 99.6 | 0.69 |

TABLE II

| Coating Number | DIR Compound | Quantity (mg/m²) | ΔAMT 35 sys Relative to Comparison 17 | gamma "causer" / gamma "receiver" |
|---|---|---|---|---|
| Comparison 17 | E | 60 | check | 1.40 |
| Comparison 18 | I | 95 | −1.6 | 1.15 |
| Comparison 19 | J | 86 | +1.2 | 1.57 |
| Comparison 20 | 14 | 75 | +1.5 | 1.34 |
| Invention 21 | 16 | 91 | +1.8 | 1.57 |
| Invention 22 | 18 | 43 | −1.6 | 0.81 |
| Invention 23 | 2 | 60 | 0.0 | 1.12 |

Comparative DIR compounds

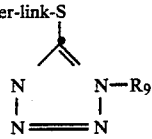

coupler-link-S attached to tetrazole with N—R₉

| Coupler | Link | R₉ | (Source) |
|---|---|---|---|
| 1-hydroxy-2-naphthamide with OC₁₄H₂₉-n phenyl | none | phenyl — A | #16 of U.S. Pat. No. 3,227,554 |
| " | none | CH₂(CH₂)₅CH₃ — B | within U.S. Pat. No. 3,227,554 |
| " | none | phenyl-OCH₂CH₃ — C | within U.S. Pat. No. 3,227,554 |
| " | none | CH₂-phenyl-OCH₃ — D | #15 of Belgian Patent 789,595 |

Comparative DIR compounds coupler-link-S

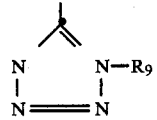

| Coupler | Link | R₉ | (Source) |
|---|---|---|---|
| " | -O-[phenyl with NO₂, CH₂N(CH(CH₃)₂)-C(=O)-] | phenyl E | #4 of U.S. Pat. No. 4,248,962 |
| " | " | $CH_2(CH_2)_5CH_3$ F | #22 of U.S. Pat. No. 4,248,962 |
| " | " | phenyl-OCH₂CH₃ G | #8 of U.S. Pat. No. 4,248,962 |
| " | -O-[phenyl with NO₂, N(CH(CH₃)₂)-C(=O)-] | phenyl I | #6 of U.S. Pat. No. 4,248,962 |
| " | -O-[phenyl with NO₂, CH₂-] | phenyl J | Within U.S. Pat. No. 4,409,323 |
| (CH₃)₃C-C(=O)-CH(-)-C(=O)-[phenyl with Cl, NH-SO₂-C₁₆H₃₃-n] | -O-[phenyl with NO₂, CH₂-N(C₂H₅)-C(=O)-] | phenyl H | #C-1 of EPA 255,085 |

The following compounds of the invention can be prepared by methods as or similar to those described. The compounds can be tested in a photographic element as described in Example 1: (Numbers indicate compound numbers)

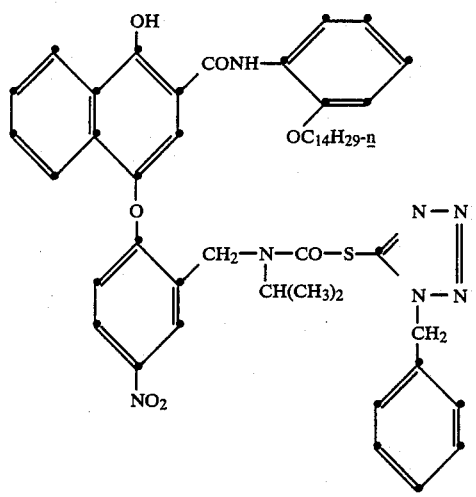
1.
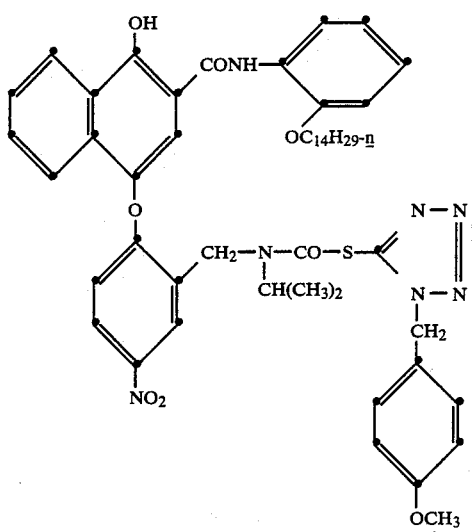
2.
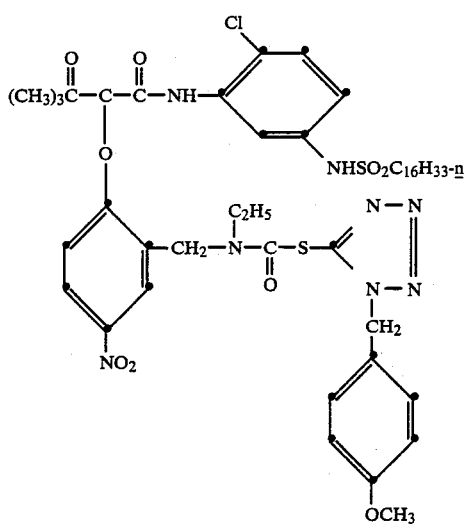
3.

4.
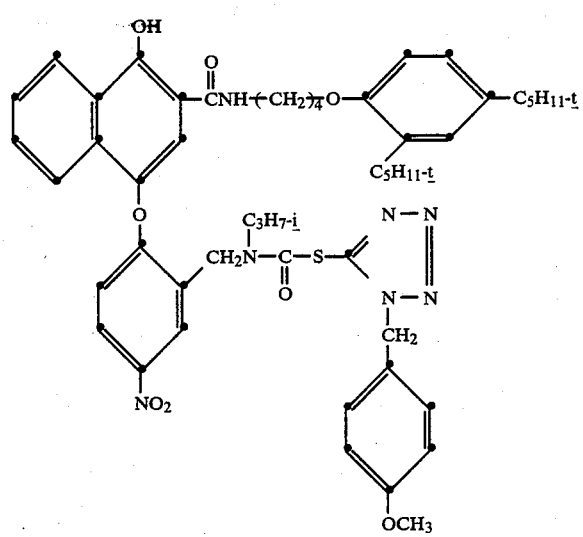
5.
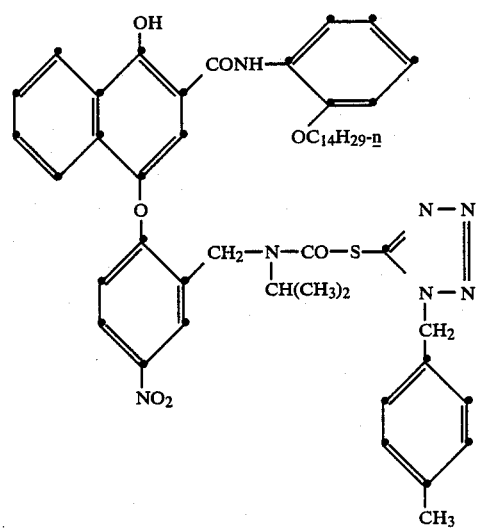
6.
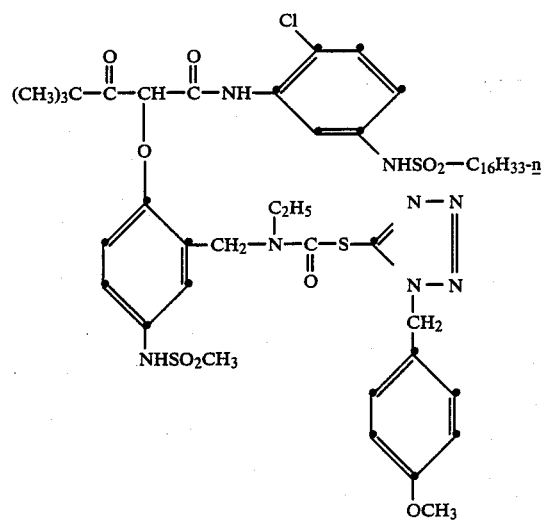

-continued
7.
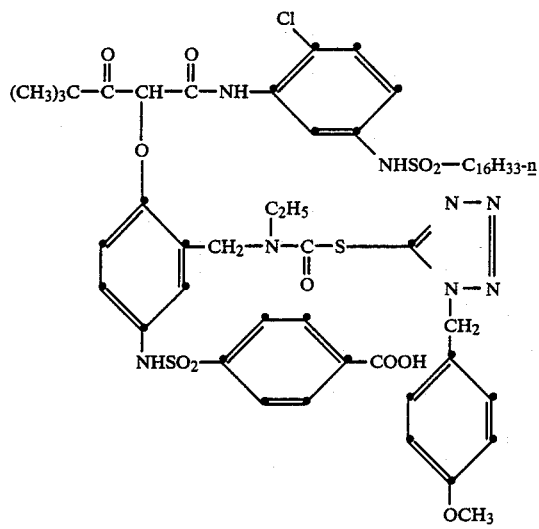
8.
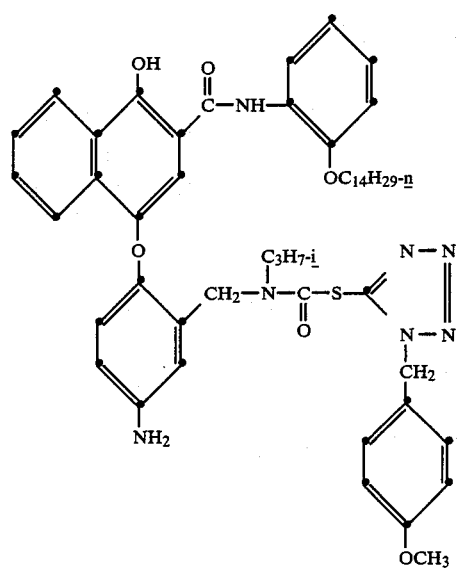
9.
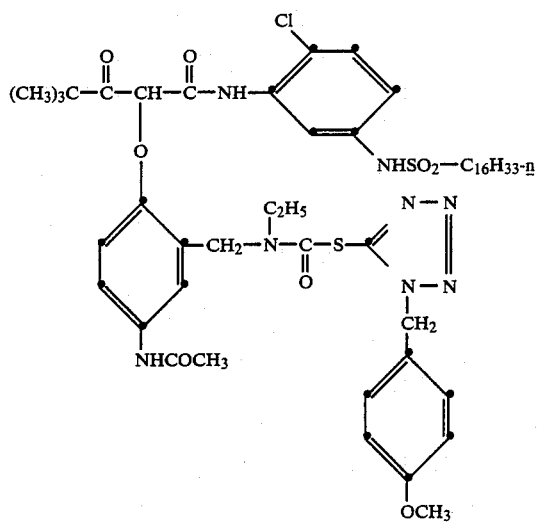

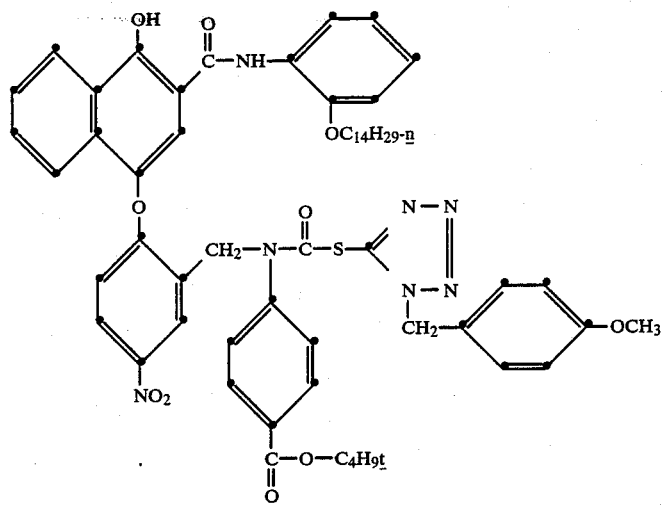
10.
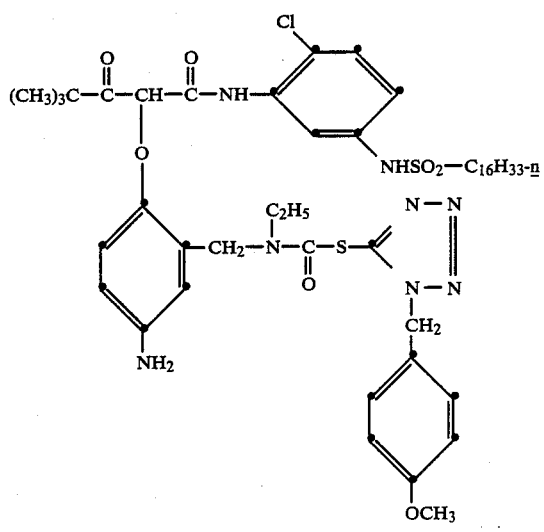
11.
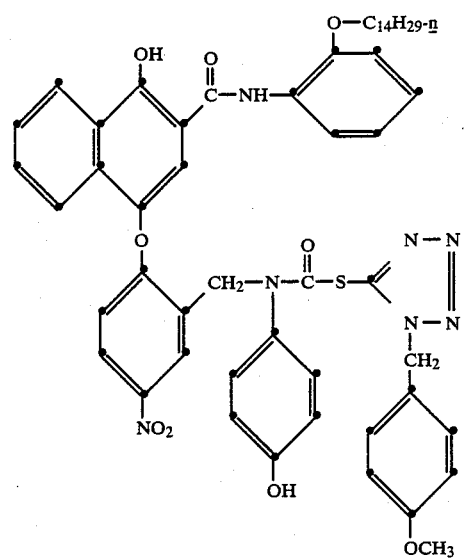
12.

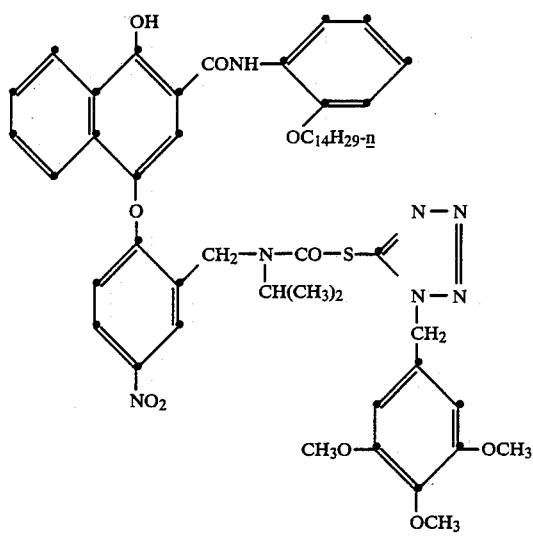
13.
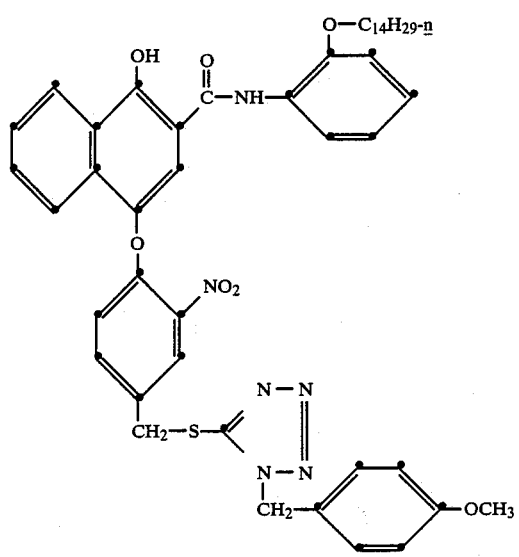
14.
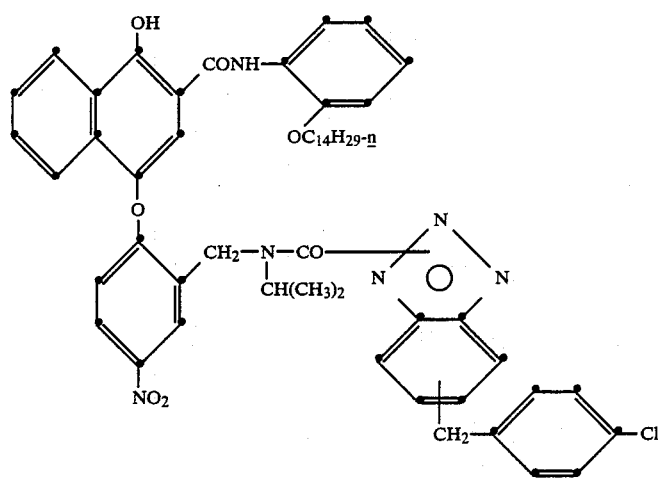
15.

16.
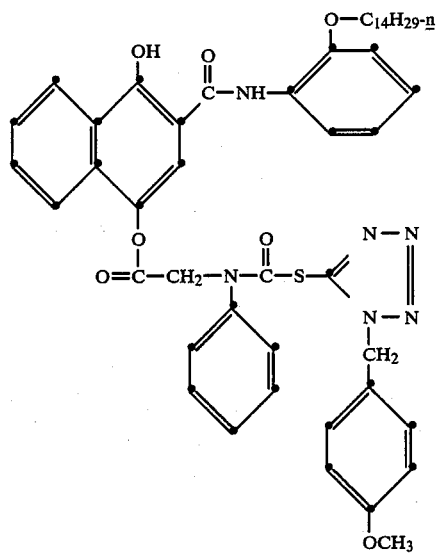
17.
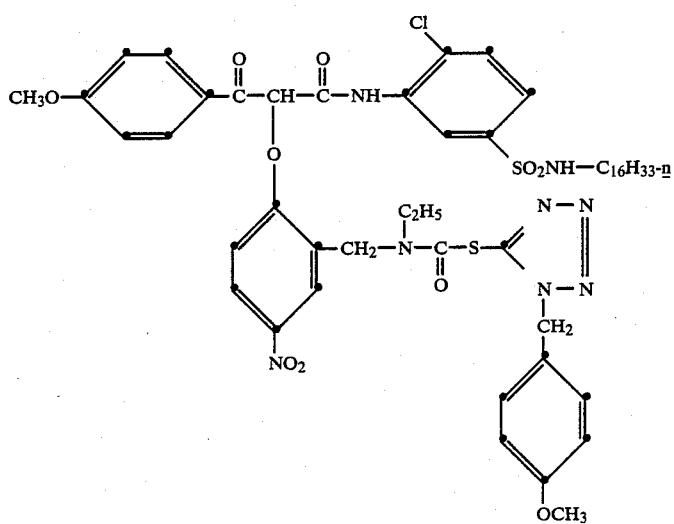
18.
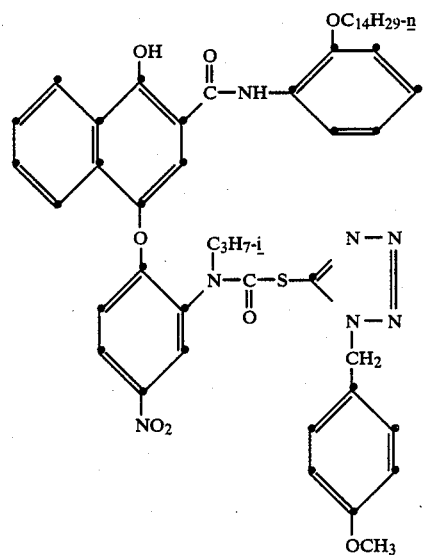

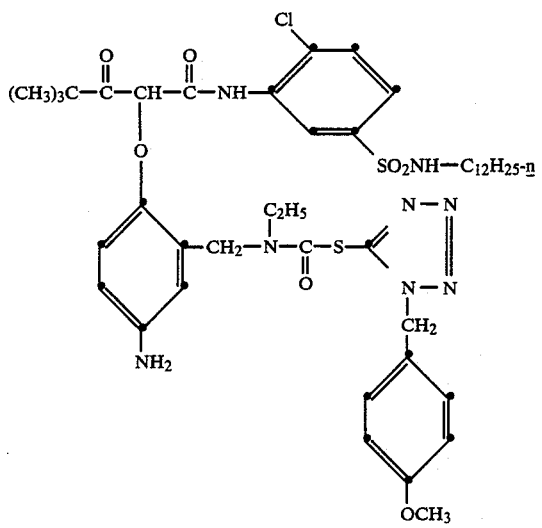
19.
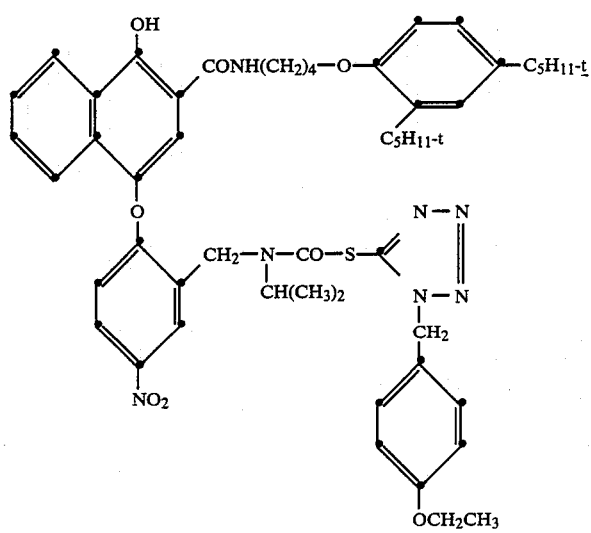
20.
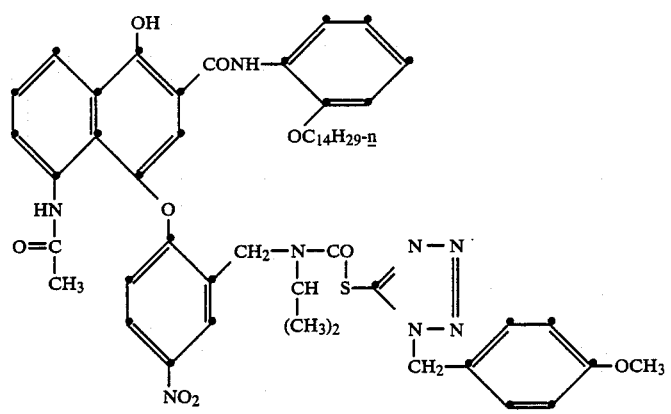
21.

22.
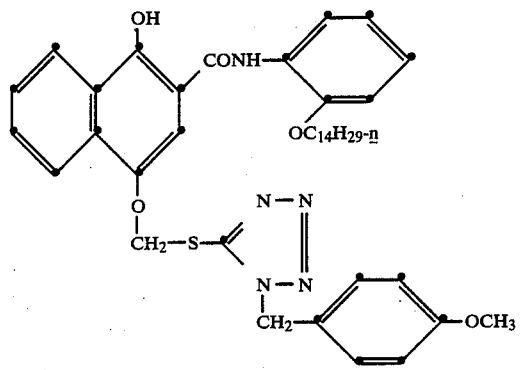
23.
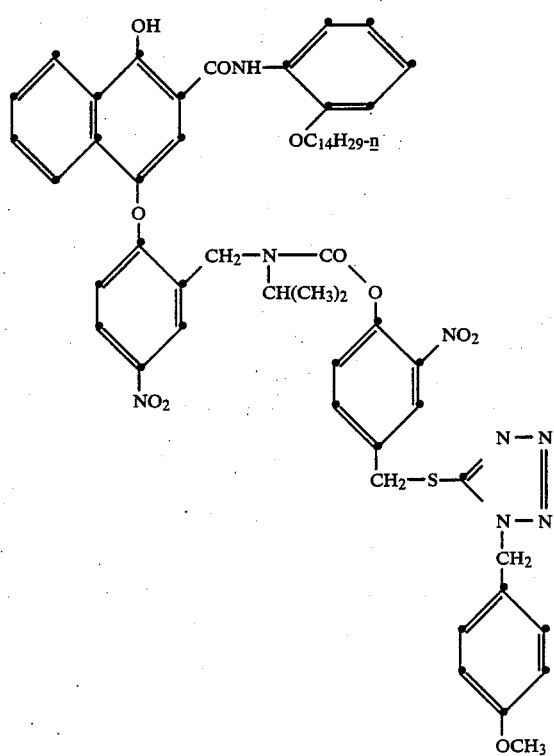
24.
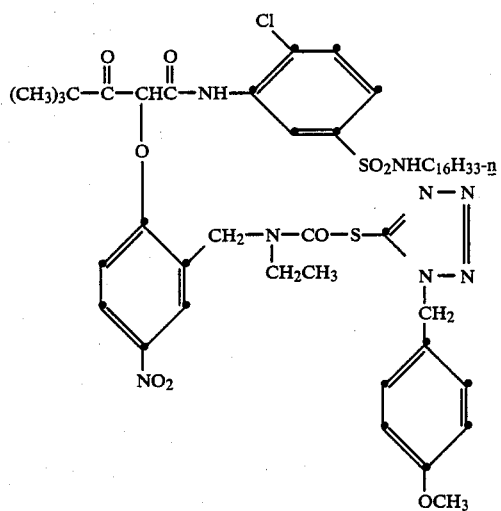

-continued
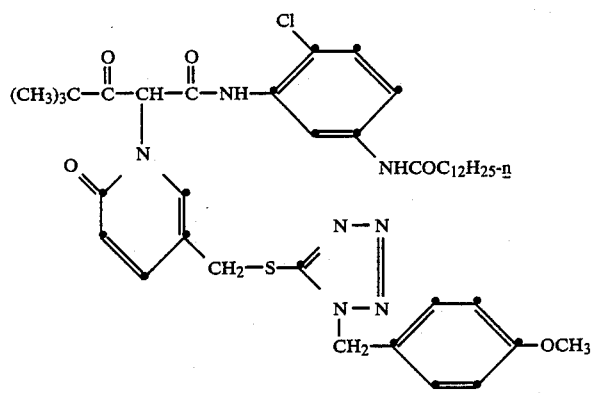
25.
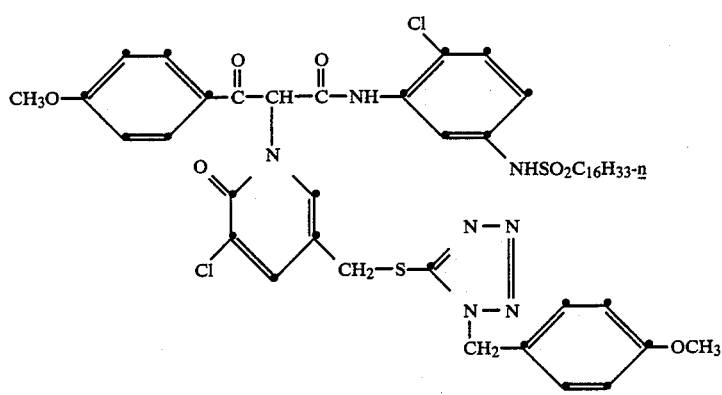
26.
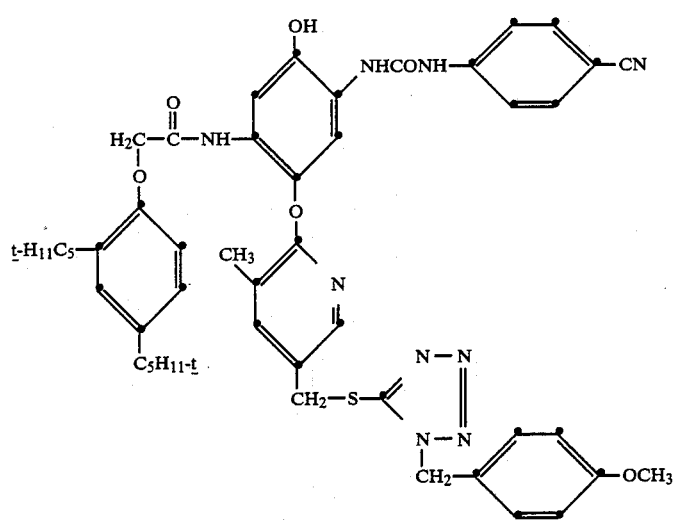
27.

28.
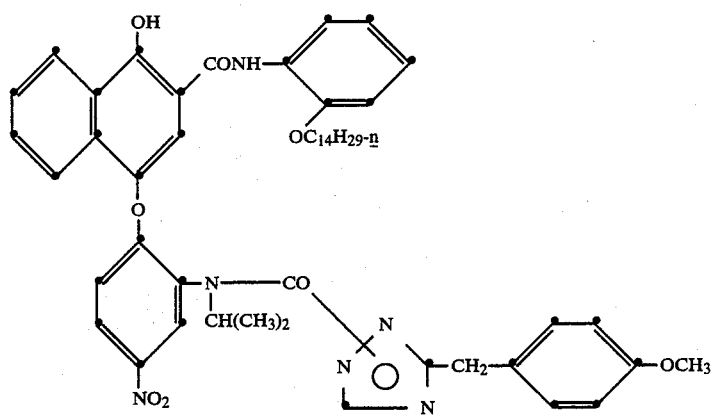
29.
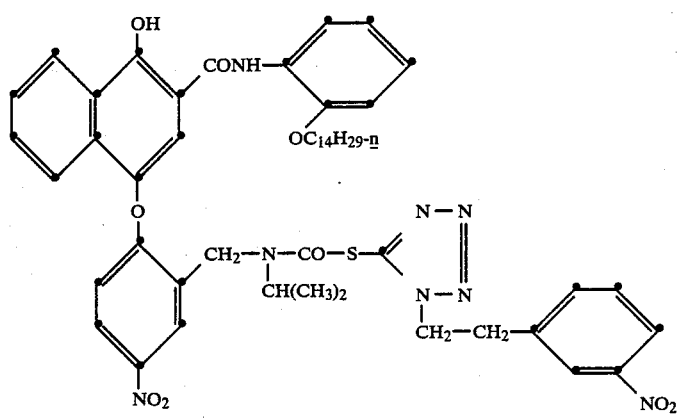
30.
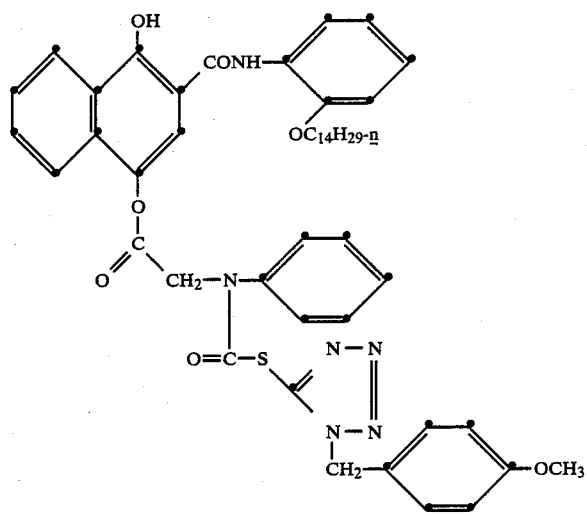

31.
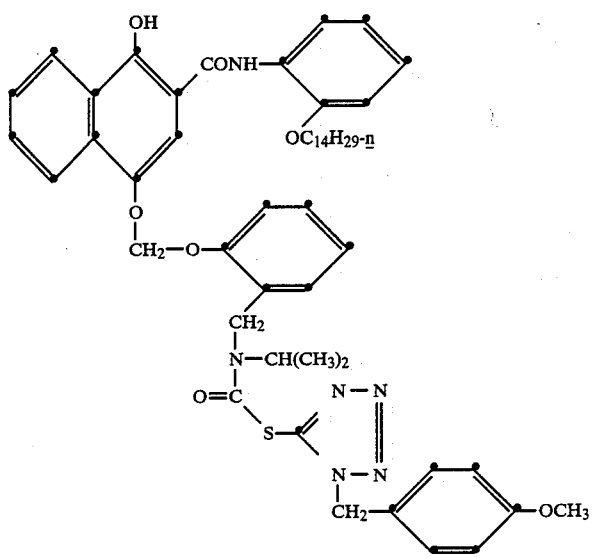
32.
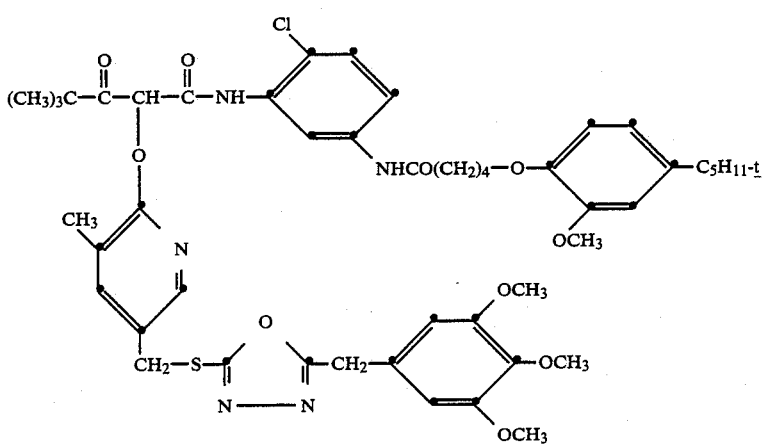
33.
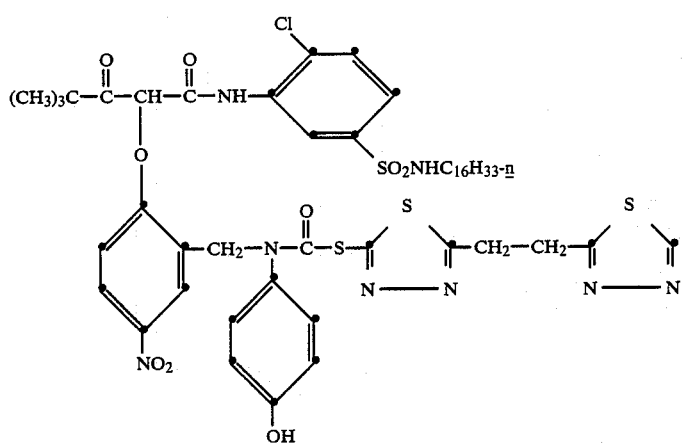

-continued
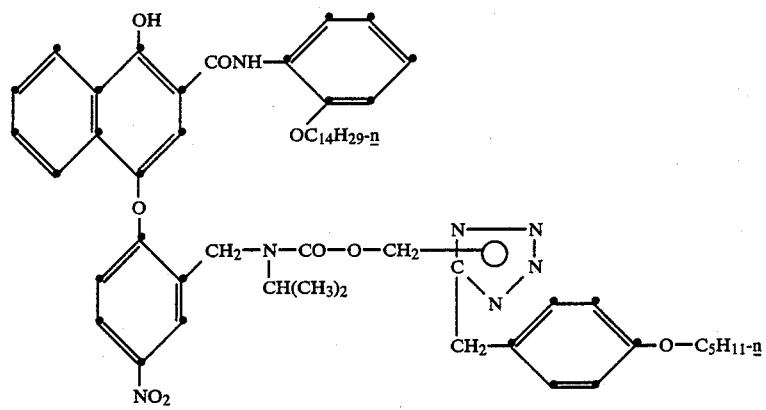
34.
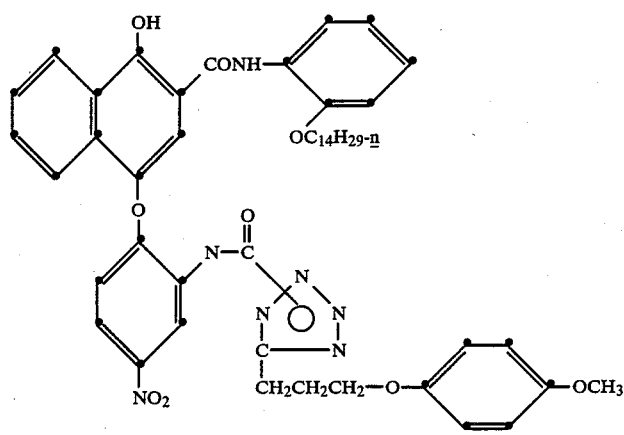
35.
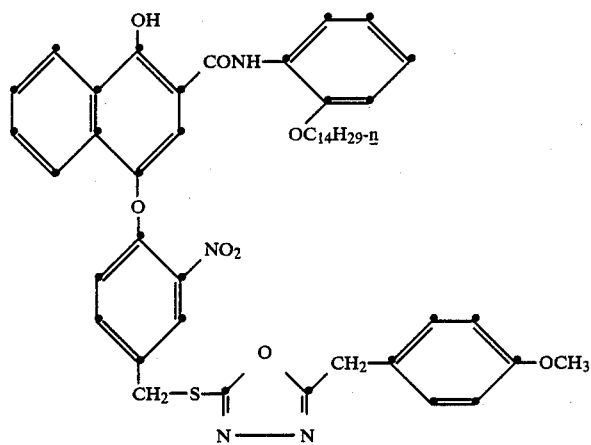
36.

37.
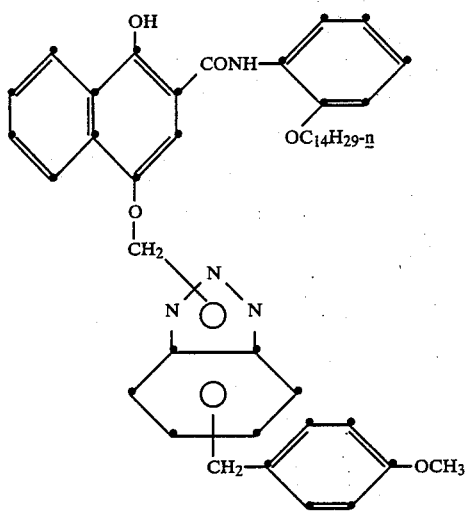
38.
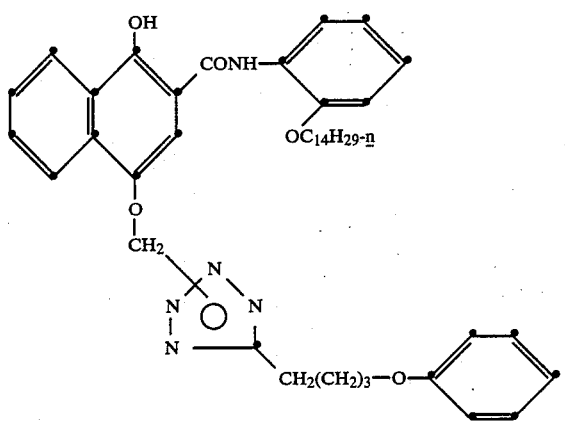
39.
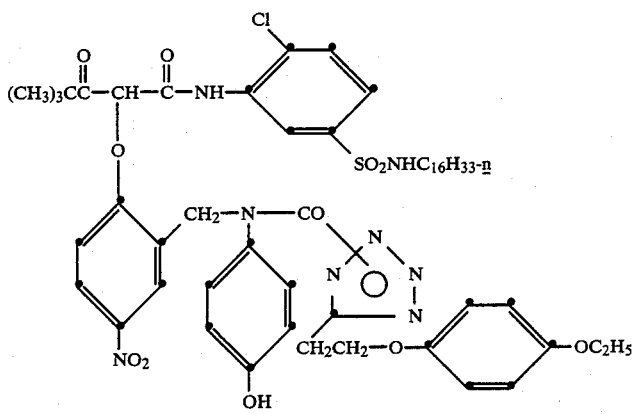

-continued
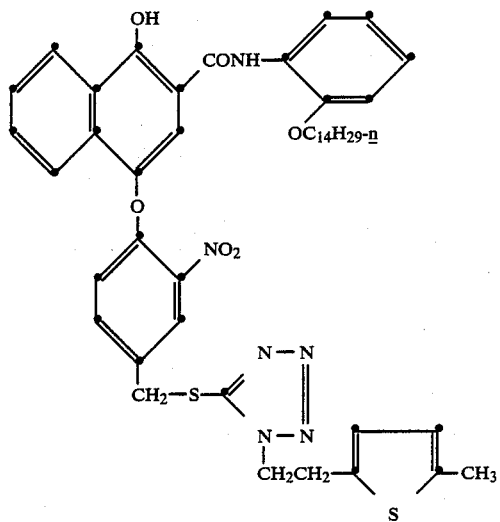
40.
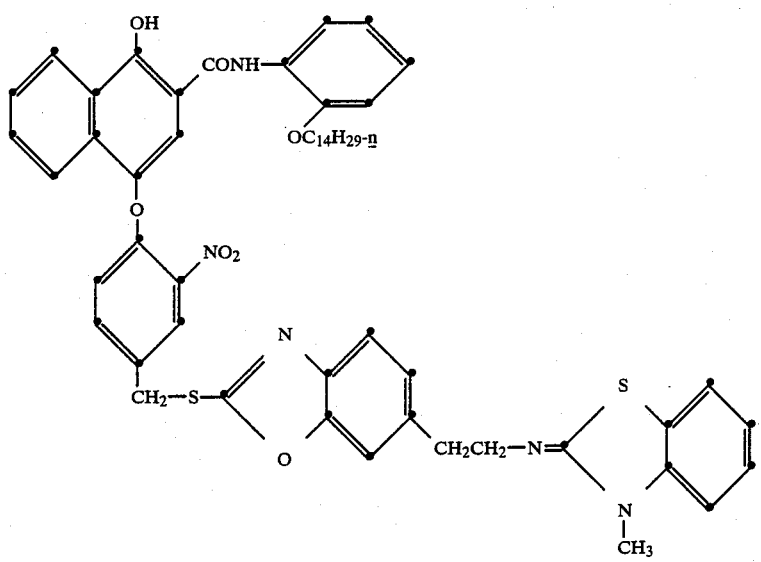
41.

42.
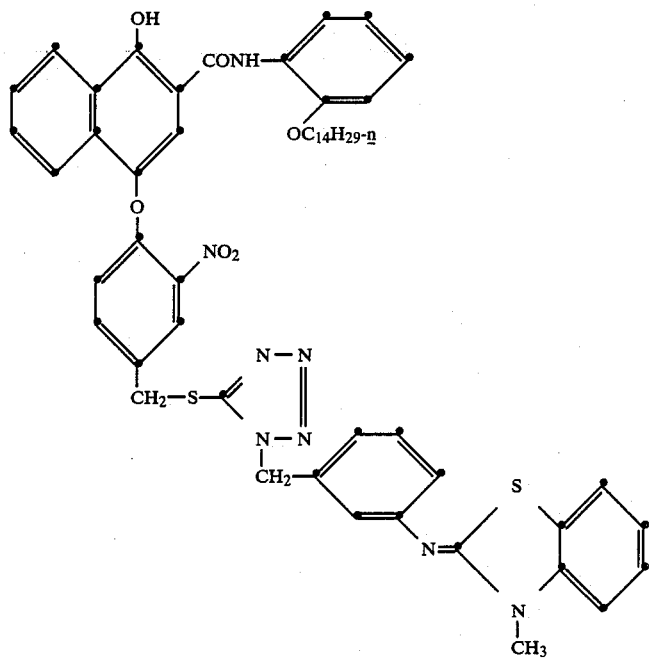
43.
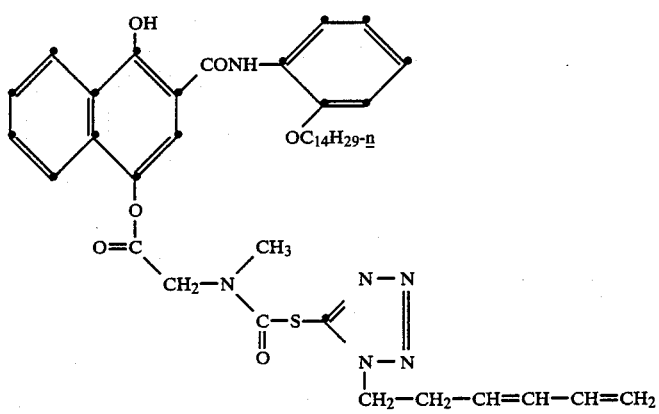
44.
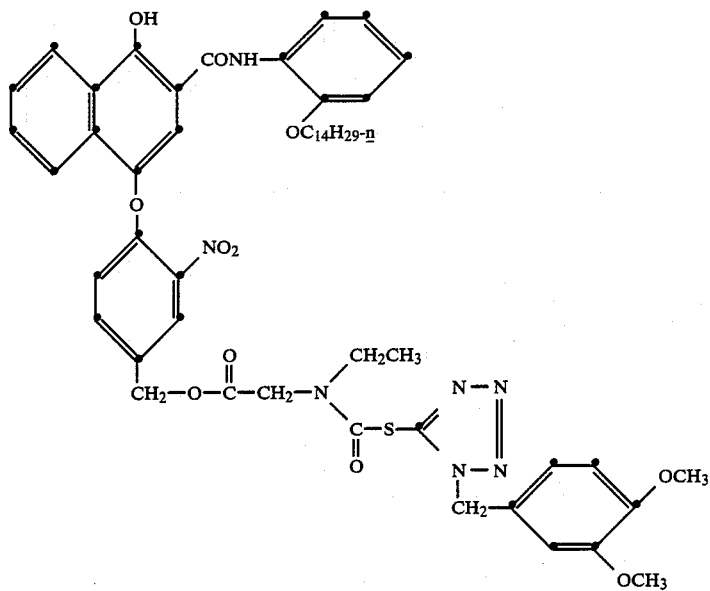

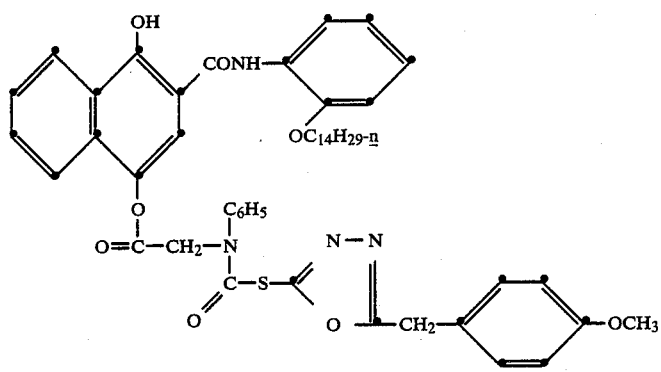
45.
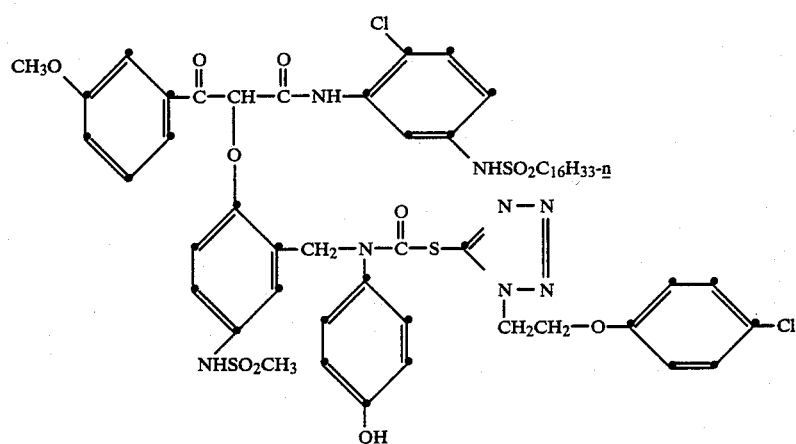
46.
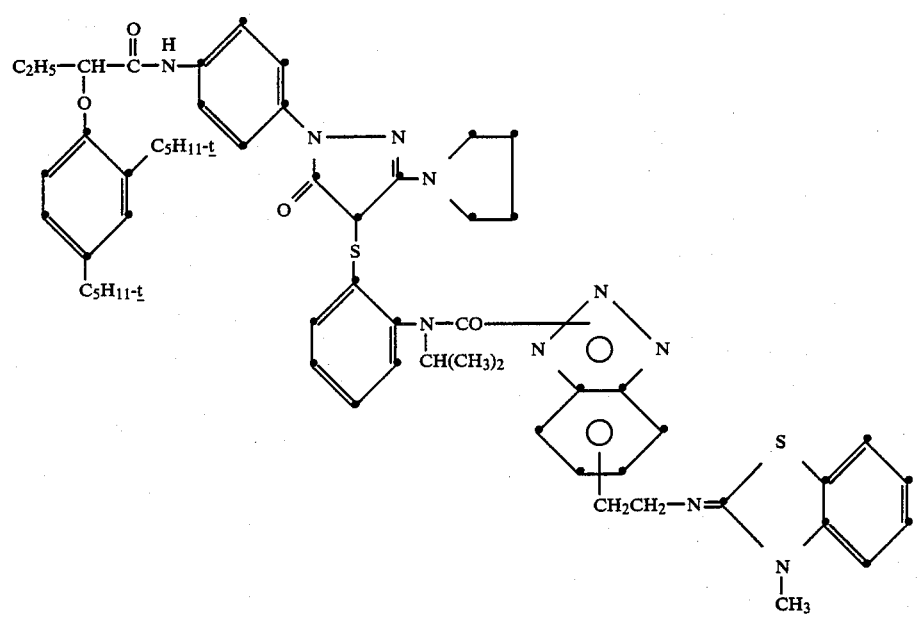
47.

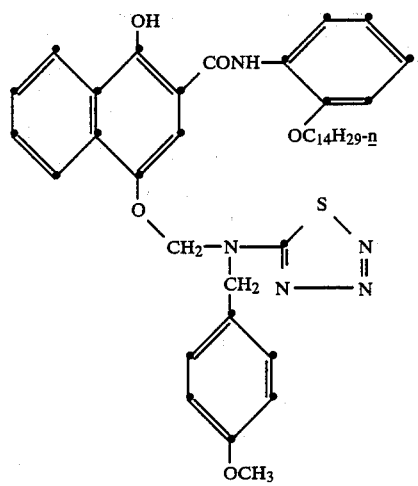
48.
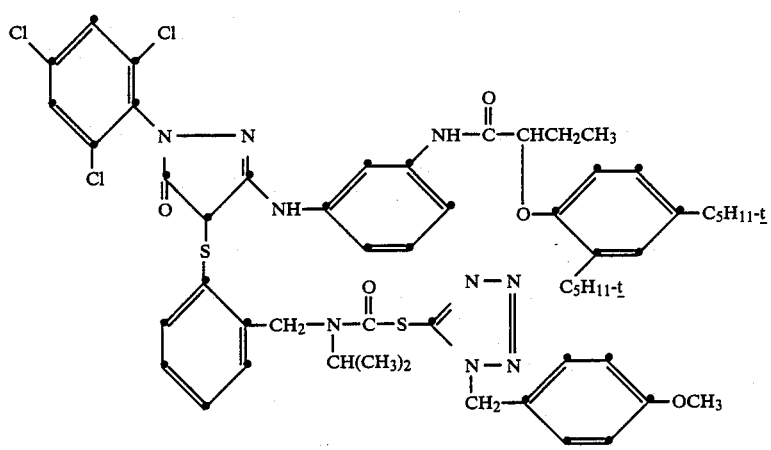
49.
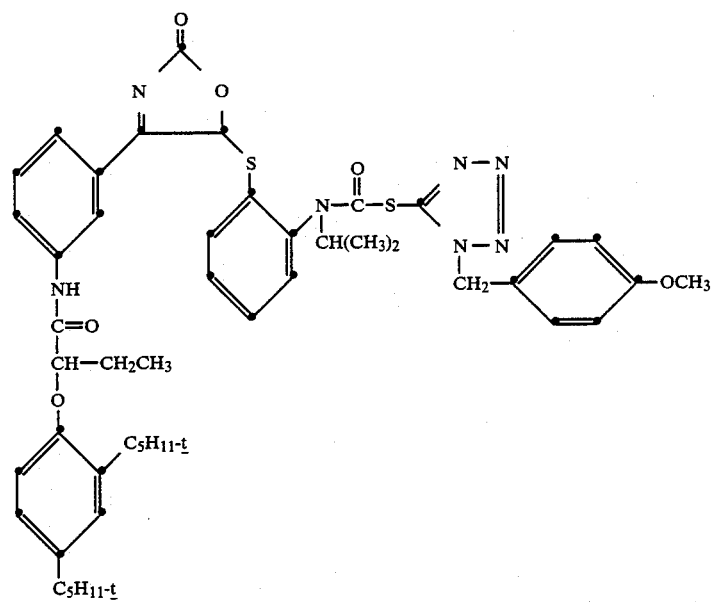
50.

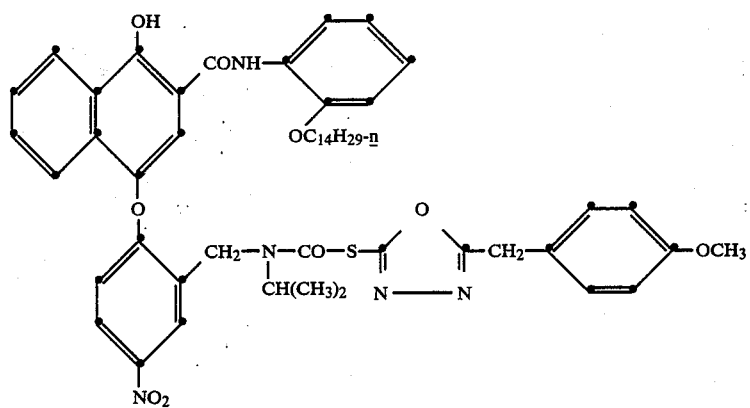
51.
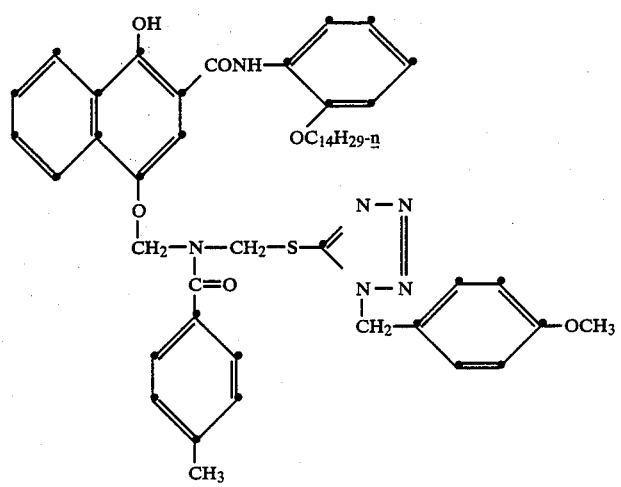
52.
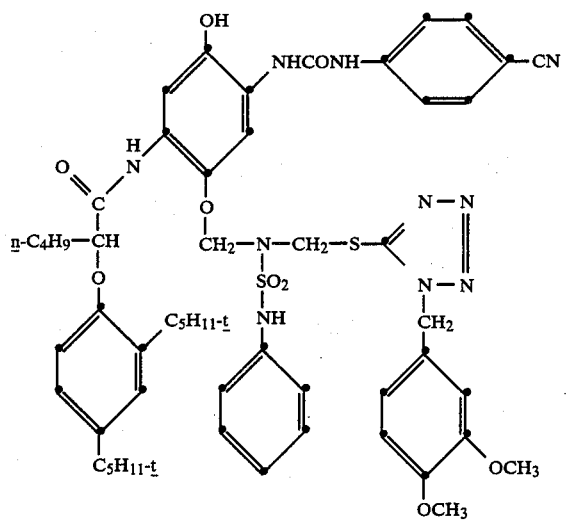
53.

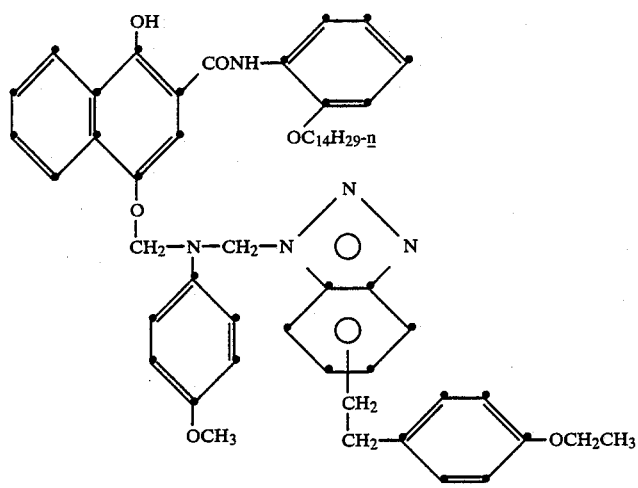
54.
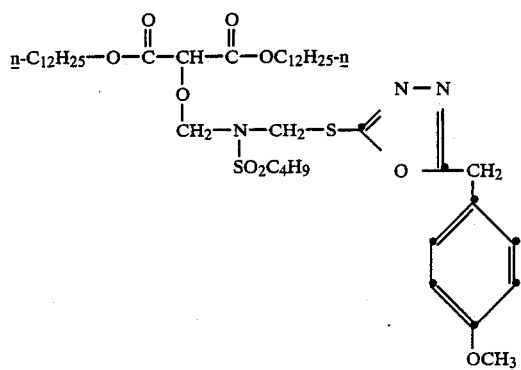
55.
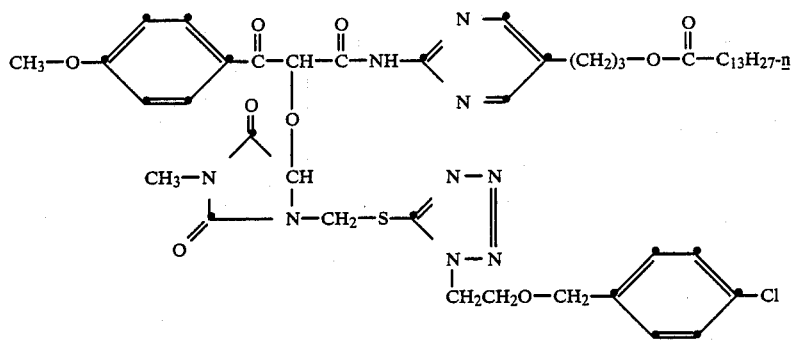
56.

-continued
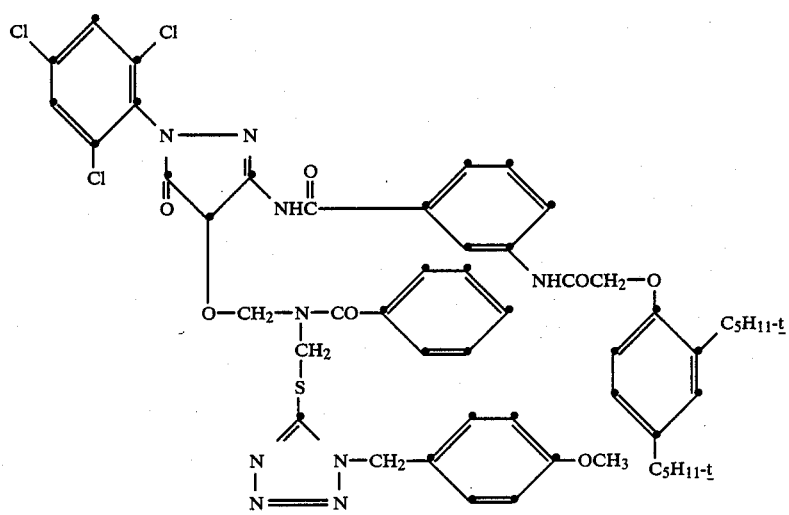
57.
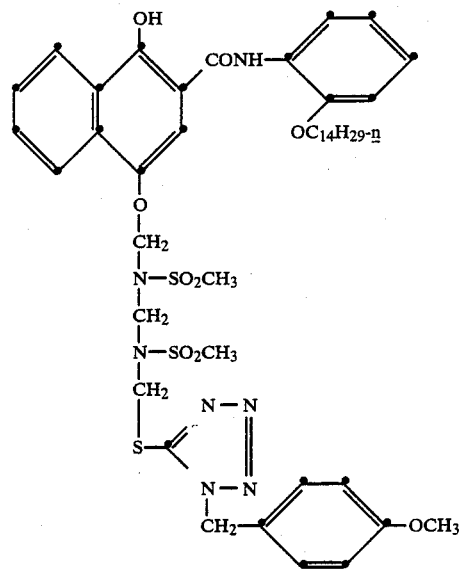
58.

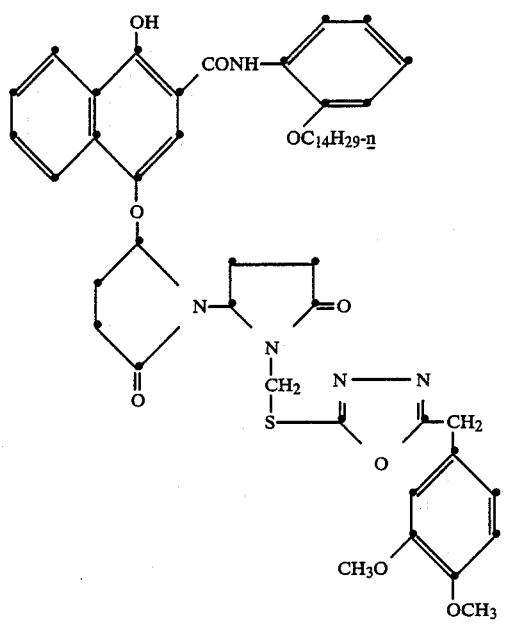
59.
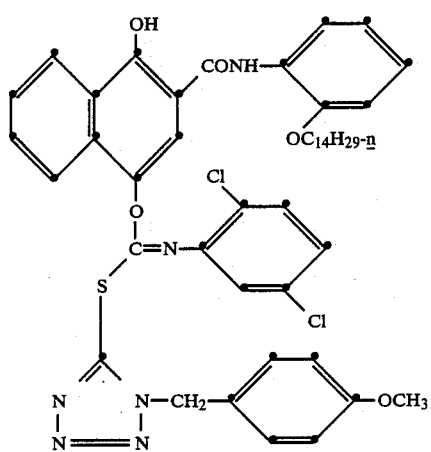
60.
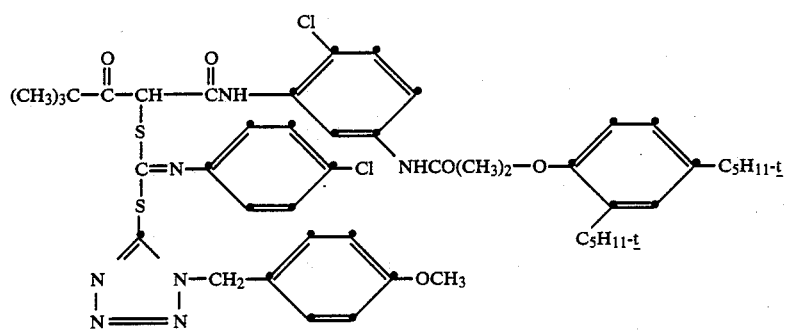
61.

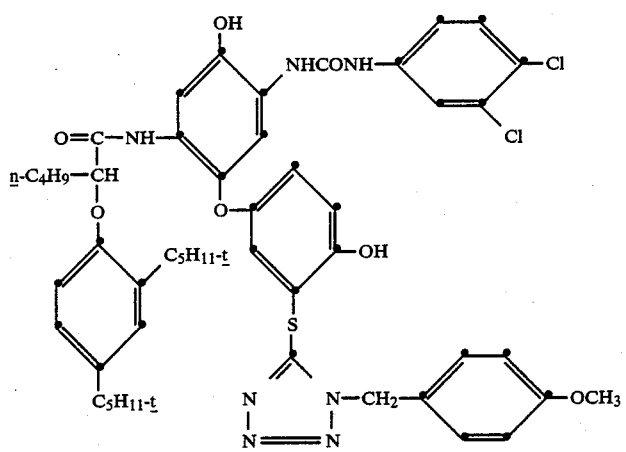
62.
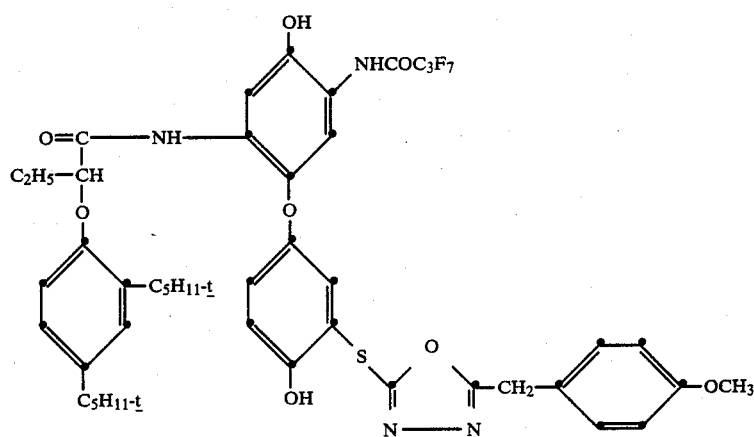
63.
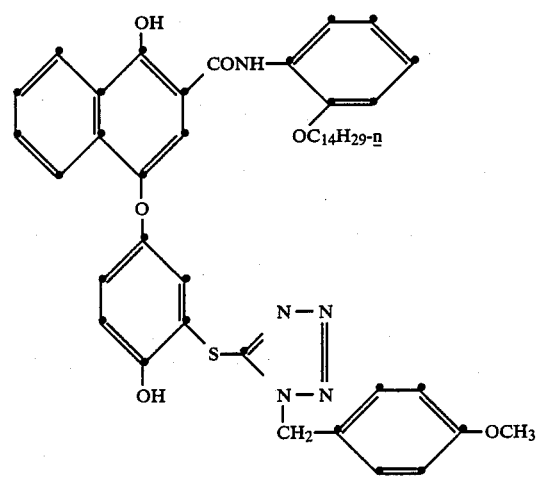
64.

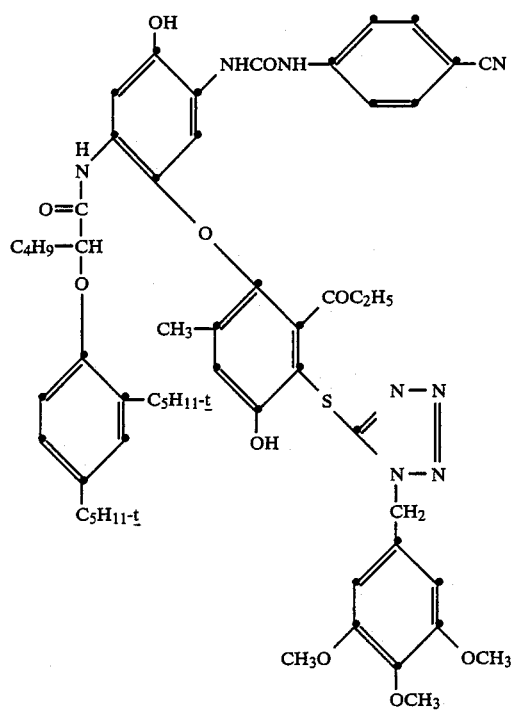
65.
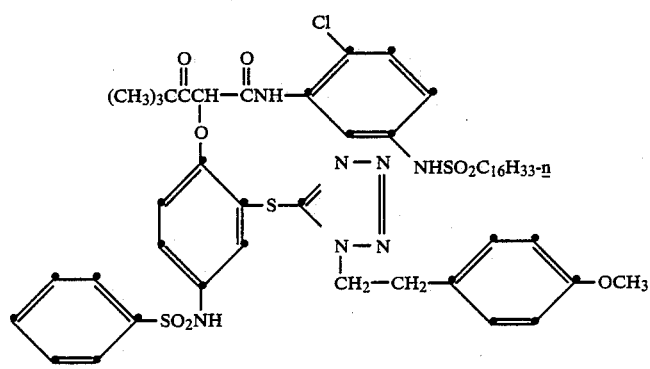
66.
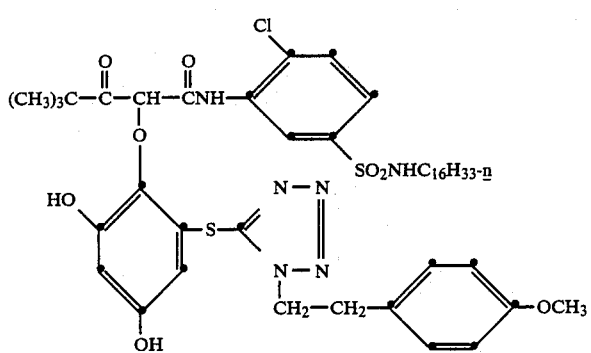
67.

-continued
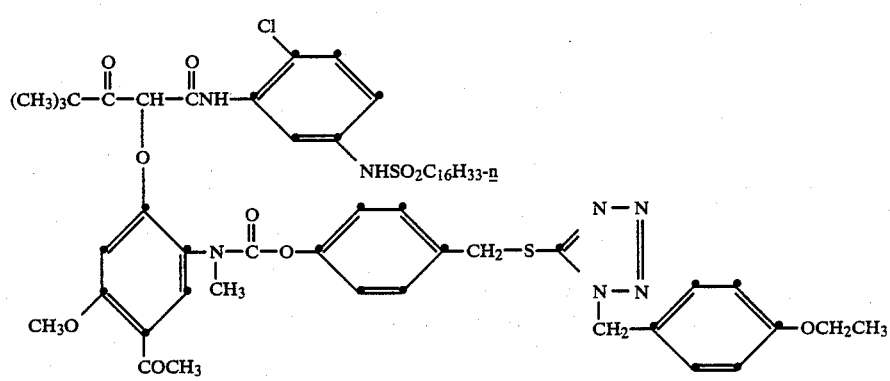
68.
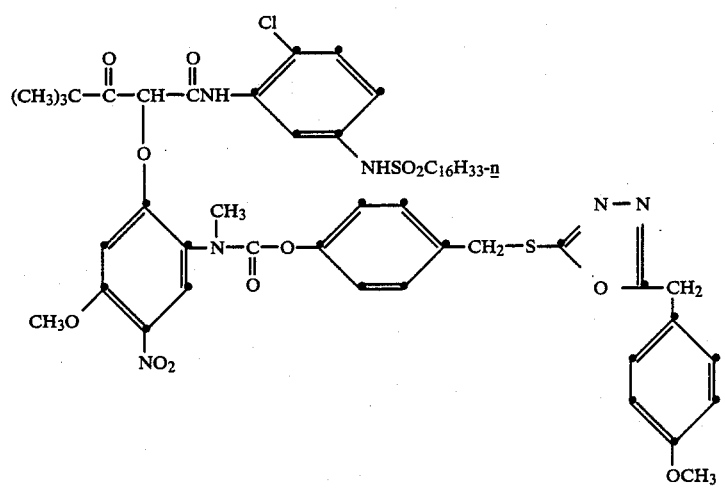
69.
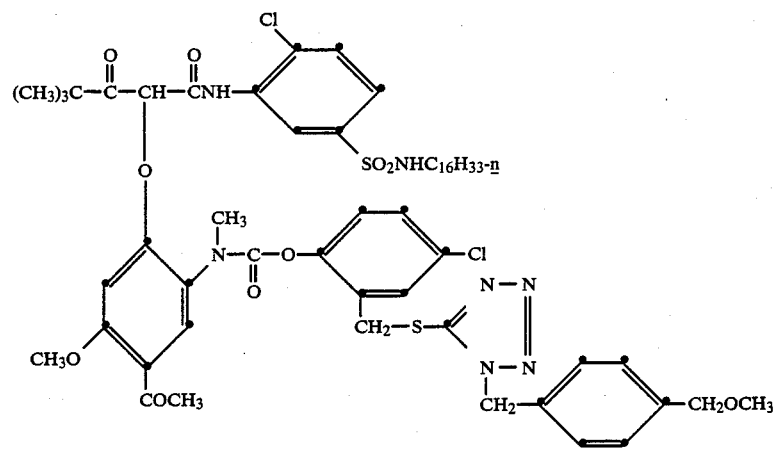
70.

-continued
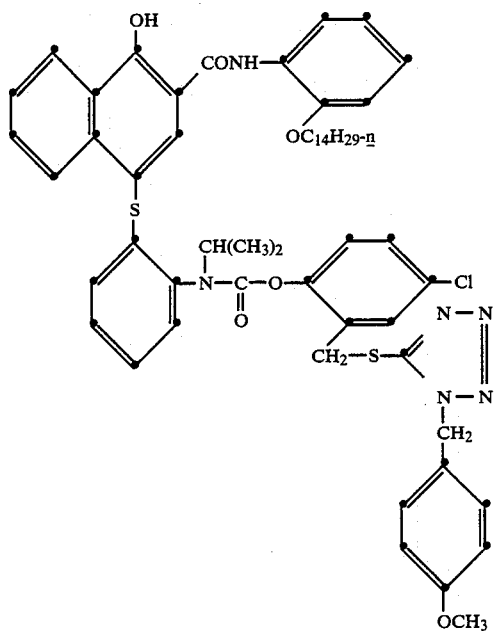
71.
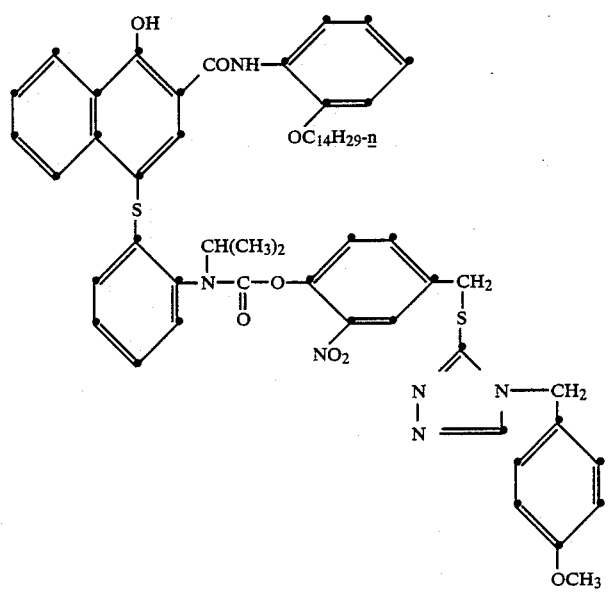
72.

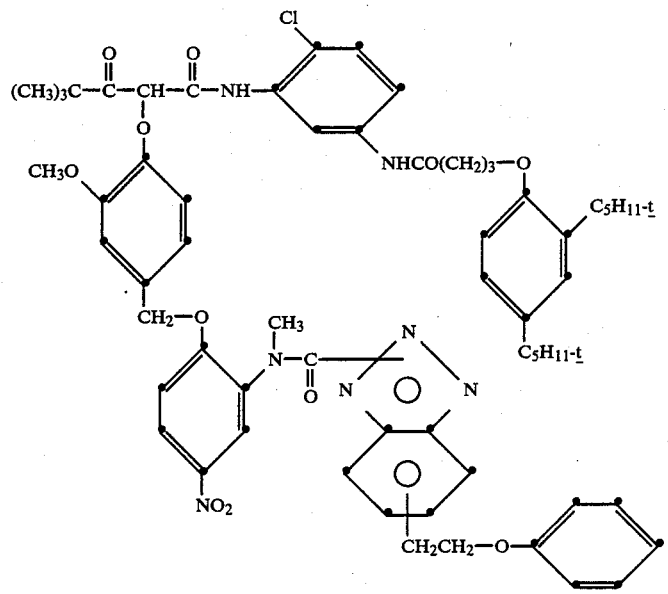
73.
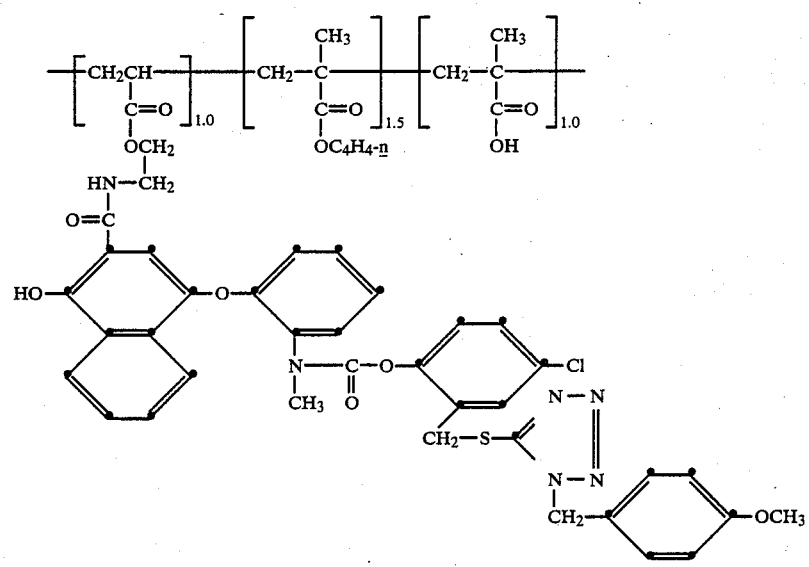
74.

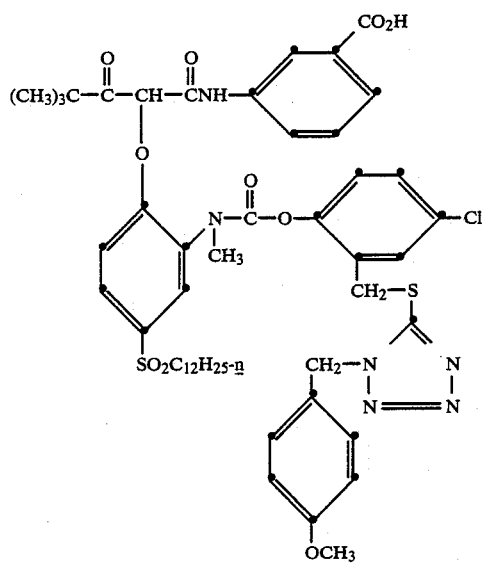
75.
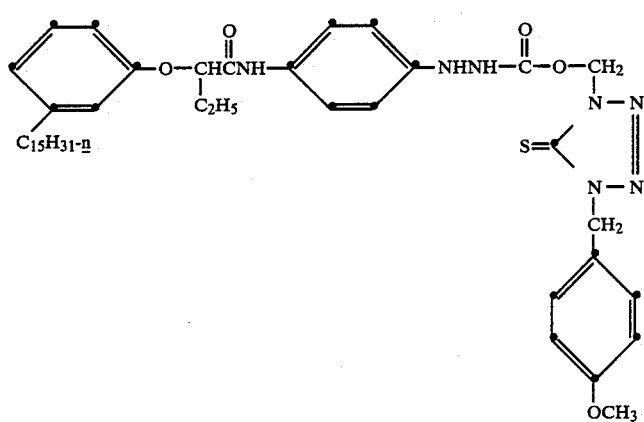
76.
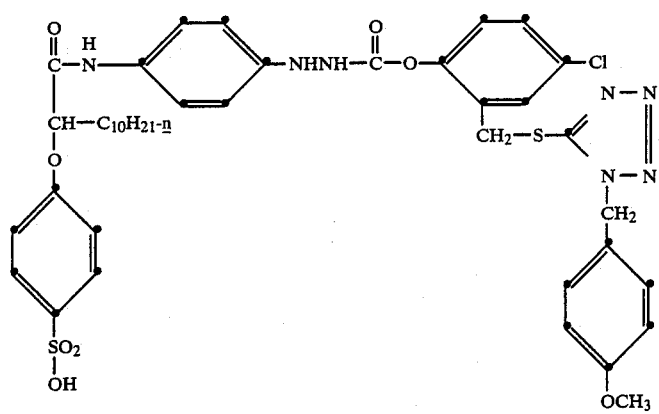
77.

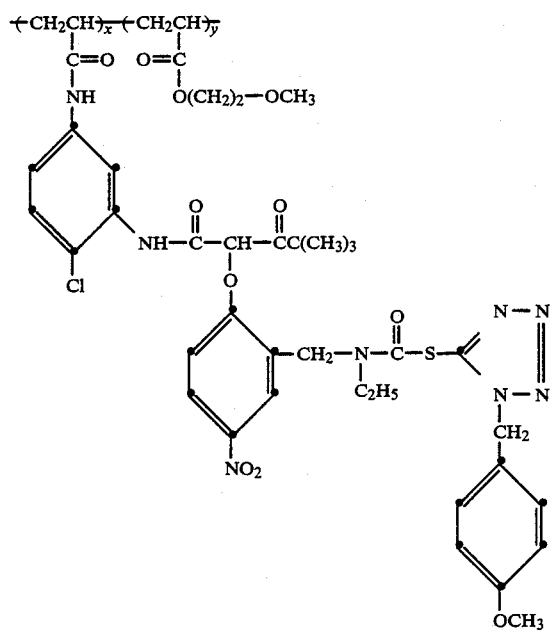
78.
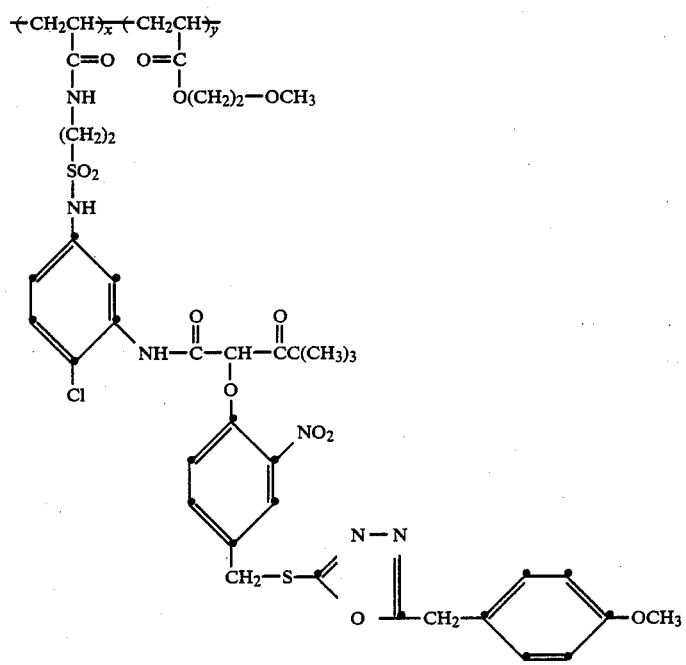
79.

80.
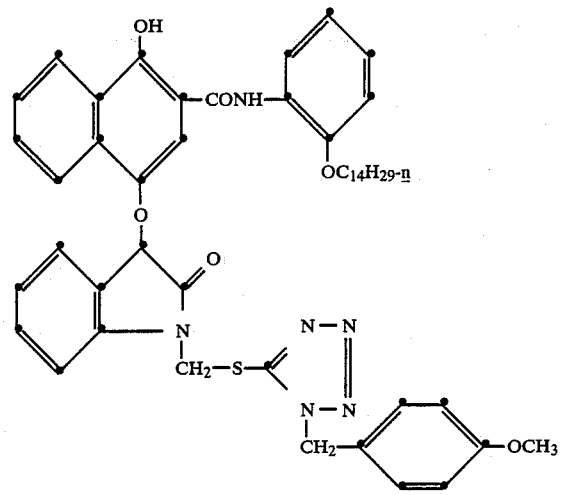
81.
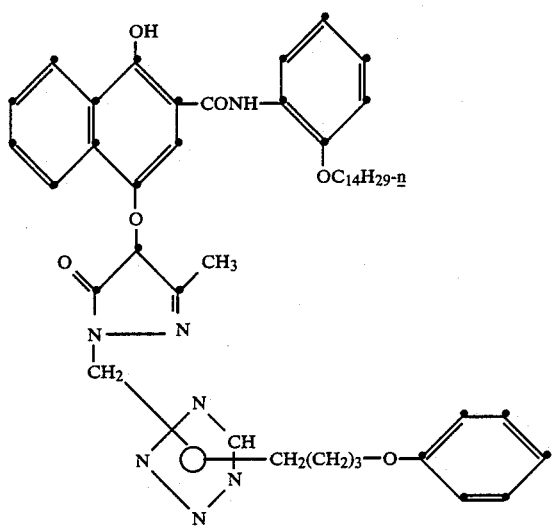
82.
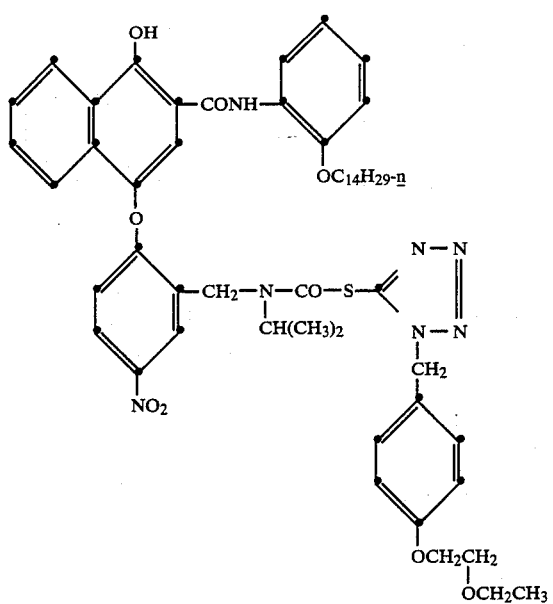

-continued

83.

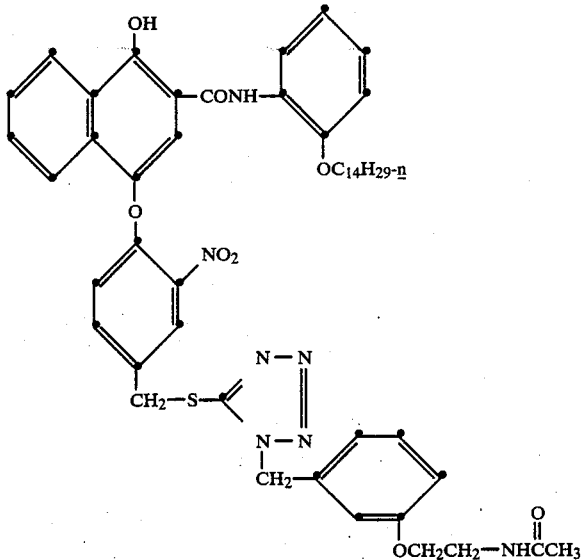

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and a development inhibitor releasing coupler comprising a coupler moiety bonded to at least one timing group that enables timing of release of a releasable development inhibitor moiety wherein the releasable development inhibitor moiety contains a —CH$_2$—Q group that is bonded directly to the inhibitor moiety and that is a group enabling, upon exposure and processing of the element, reduced interlayer interimage effect without reduced image acutance in the emulsion layer, and wherein the inhibitor moiety does not decompose during processing.

2. A photographic element as in claim 1 wherein the development inhibitor releasing coupler is represented by the formula:

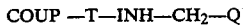
COUP —T—INH—CH$_2$—Q wherein
COUP is a coupler moiety;
T is a timing group bonded to the coupler moiety at a coupling position and enabling timed release of —INH—CH$_2$—Q from the coupler moiety upon exposure and processing of the element;
INH—CH$_2$—Q is a development inhibitor moiety wherein
Q is a ballasting group.

3. A photographic element as in claim 1 wherein the development inhibitor releasing coupler is represented by the formula:

COUP—T—INH—CH$_2$—Q wherein
COUP is a coupler moiety;
T is a timing group bonded to the coupler moiety at a coupling position and enabling timed release of —INH—CH$_2$—Q from the coupler moiety upon exposure and processing of the element;
INH—CH$_2$—Q is a development inhibitor moiety wherein
Q is a ballasting group (i) having a molecular weight greater than 70 mass units, (ii) contains no ionized groups during processing, (iii) does not substantially decompose during processing, and (iv) contains at least one C=C or C=N double bond.

4. A photographic element as in claim 1 wherein the releasable development inhibitor moiety is selected from the group consisting of

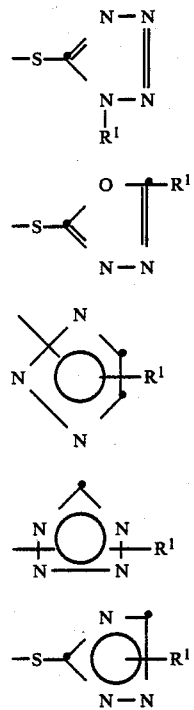

-continued

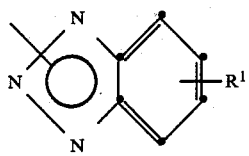

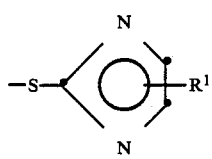

wherein R¹ is

5. A photographic element comprising a support bearing at least one photographic silver halide emulsion layer and a development inhibitor releasing coupler represented by the formula:

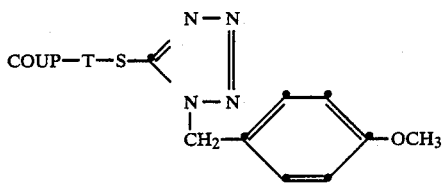

wherein COUP is a coupler moiety and T is a releasable timing group bonded to the coupler moiety at the coupling position.

6. A photographic element as in claim 1 wherein the timing group is a group capable of an intramolecular nucleophilic displacement of the releasable development inhibitor moiety.

7. A photographic element as in claim 1 wherein the timing group involves electron transfer down a conjugated chain in which alternate single bonds and double bonds occur.

8. A photographic element as in claim 1 wherein the development inhibitor releasing coupler is

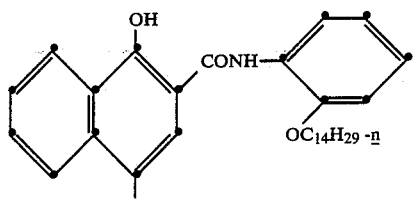

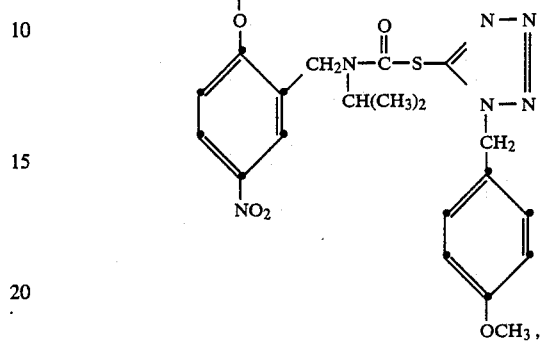

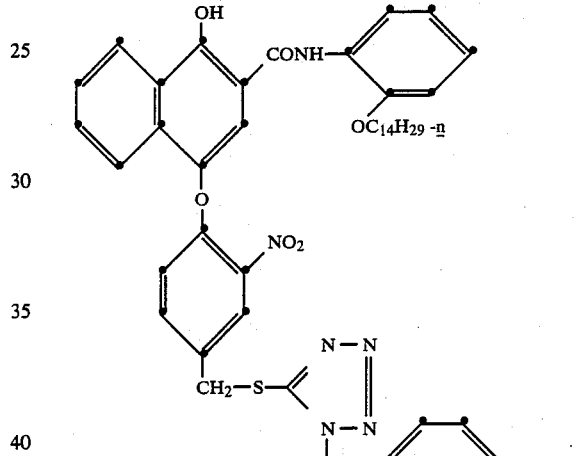

or

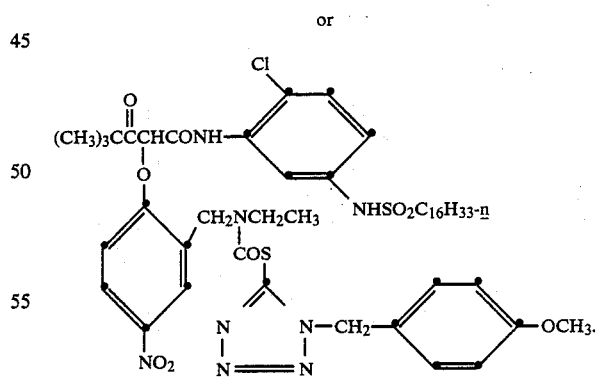

9. A process of forming a photographic image that comprises developing an exposed photographic silver halide emulsion layer with a color developing agent in the presence of a dye-forming coupler (A) and a development inhibitor releasing coupler (B) comprising a coupler moiety bonded to at least one timing group that enables timing of release of a releasable development inhibitor moiety wherein the releasable development inhibitor moiety contains a —CH$_2$—Q group that is bonded directly to the inhibitor moiety and that is a ballasting group enabling upon exposure and processing of the element reduced interlayer interimage effect without reduced image acutance in the emulsion layer.

10. A process as in claim 9 wherein the development inhibitor releasing coupler is represented by the formula:

COUP—T—INH—CH₂—Q wherein
COUP is a coupler moiety;
T is a timing group bonded to the coupler moiety at a coupling position and enabling timed release of INH—CH₂—Q from the coupler moiety upon exposure and processing of the element;
INH—CH₂—Q is a development inhibitor moiety wherein
Q is a ballasting group.

11. A process as in claim 9 wherein the releasable development inhibitor moiety is represented by the formula:

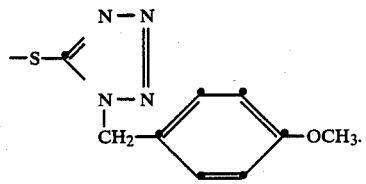

12. A photographic development inhibitor releasing coupler comprising a coupler moiety bonded to at least one timing group that enables, in a photographic silver halide element upon exposure and processing, timing of release of a releasable development inhibitor moiety wherein the releasable development inhibitor moiety contains a —CH₂—Q group that is bonded directly to the inhibitor moiety and that is a ballast group enabling upon exposure and processing of the element reduced interlayer interimage effect without reduced image acutance in the photographic element.

13. A photographic development inhibitor releasing coupler represented by the formula:

COUP—T—INH—CH₂—Q wherein
COUP is a photographic coupler moiety;
T is a timing group bonded to the coupler moiety at a coupling position and enabling timed release of —INH—CH₂—Q from the coupler moiety upon exposure and processing of a photographic element containing the development inhibitor releasing coupler;
INH—CH₂—Q is a development inhibitor moiety, wherein
Q is a ballasting group.

14. A photographic development inhibitor releasing coupler as in claim 13 wherein Q is a group (i) having a molecular weight greater than 70 mass units, and containing at least one C=C or C=N double bond, and when in a photographic silver halide element during photographic processing (ii) contains no ionized groups and (iii) does not substantially decompose.

* * * * *

UNITED STATES PATENT AND TRADEMARK OFFICE
CERTIFICATE OF CORRECTION

PATENT NO. : 4,962,018

DATED : October 9, 1990

INVENTOR(S) : Richard P. Szajewski, et al

Page 1 of 5

It is certified that error appears in the above-indentified patent and that said Letters Patent is hereby corrected as shown below:

Column 2, line 15, "Layer at" should read --layer, at--.

Column 2, line 26, "couple" should read --coupler--.

Column 2, line 58, "pO" should be deleted and X should begin a new paragraph at the left margin.

Column 3, line 61, "color Forming" should read --color-forming--.

Column 4, line 59, after configuration, --of-- should be inserted.

Column 5, line 58, "Free" should read --free--.

Column 6, line 2, after Representative, "." should be deleted.

Column 6, line 43, "Formed" should read --formed--.

Column 7, lines 37-38, "pre-Ferred" should read --preferred--.

Column 7, line 40, "modiFy" should read --modify--.

Column 7, line 41, "isplacement" should read --displacement--.

Column 8, line 45, "s" should read --a--.

Column 10, line 15, "e" should read --a--.

Column 10, line 27, "benzoylacetanilidesnd" should read --benzoylacetanilides and--.

UNITED STATES PATENT AND TRADEMARK OFFICE
CERTIFICATE OF CORRECTION

PATENT NO. : 4,962,018
DATED : October 9, 1990
INVENTOR(S) : Richard P. Szajewski, et al It is certified that error appears in the above-indentified patent and that said Letters Patent is hereby corrected as shown below:

Column 12, line 7, "Nos." should read --No.--.

Column 12, line 10, "reactiou" should read --reaction--.

Column 12, line 30, "alkyl or" should read --alkyl of--.

Column 14, approximate line 57, that part of formula reading  should read 

Column 15, second formula, that part of formula reading 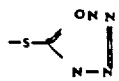 should read 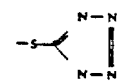

Column 21, first formula, that part of formula reading 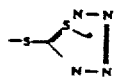 should read 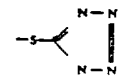

Columns 27-28, fourth line of formulas, that part of formula on right reading  should read 

UNITED STATES PATENT AND TRADEMARK OFFICE
CERTIFICATE OF CORRECTION

PATENT NO. : 4,962,018

DATED : October 9, 1990

INVENTOR(S) : Richard P. Szajewski, et al

Page 3 of 5

It is certified that error appears in the above-indentified patent and that said Letters Patent is hereby corrected as shown below:

Column 36, line 29, "layer" should read --layers--.

Column 39, line 39, "Previous" should read --previous--.

Column 40, line 49, "0.8" should read --0.84--.

Column 40, line 54, "our" should read --four--.

Column 40, line 61, "From" should read --from--.

Column 41, line 39, "Phosgene" should read --phosgene--.

Column 41, line 44, "(19 6" should read --(19.6--.

Column 45, line 35, "acetate." should read --acetate).--.

Column 46, line 7, "Photographic" should read --photographic--.

Column 46, line 36, "Followed" should read --followed--.

Column 46, line 46, "Prepared" should read --prepared--.

Column 46, line 62, "wer" should read --were--.

Column 48, line 51, "Film" should read --film--.

Column 48, line 52, "&o" should read --to--.

UNITED STATES PATENT AND TRADEMARK OFFICE
CERTIFICATE OF CORRECTION

PATENT NO. : 4,962,018
DATED : October 9, 1990
INVENTOR(S) : Richard P. Szajewski, et al It is certified that error appears in the above-indentified patent and that said Letters Patent is hereby corrected as shown below:

Column 48, line 53, "amma" should read --gamma--.

Column 48, line 59, "as" should read --(as--.

Column 48, line 60, "&he" should read --the--.

Columns 49-50, TABLE I, under heading CMT 16 mm, line 3, "0.56" should be the third line in the column to its right.

Columns 65-66, first formula, that part of formula reading $\overset{|}{N}H_2$ should read $\overset{|}{N}O_2$ Columns 97-98, last formula, that part of formula reading $\overset{|}{C}H_2-CH_2-$ should read $\overset{|}{C}H_2-$

UNITED STATES PATENT AND TRADEMARK OFFICE
CERTIFICATE OF CORRECTION

PATENT NO. : 4,962,018

DATED : October 9, 1990

INVENTOR(S) : Richard P. Szajewski, et al

Page 5 of 5

It is certified that error appears in the above-identified patent and that said Letters Patent is hereby corrected as shown below:

Columns 103-104, last formula, that part of formula reading $\overset{|}{O}C_4H_4\text{-}\underline{n}$ should read $\overset{|}{O}C_4H_9\underline{n}$ Signed and Sealed this Thirty-first Day of August, 1993

*Attest:*

BRUCE LEHMAN

*Attesting Officer*  *Commissioner of Patents and Trademarks*